(12) United States Patent
Kirsch et al.

(10) Patent No.: US 7,638,641 B2
(45) Date of Patent: Dec. 29, 2009

(54) TETRAHYDROPYRAN DERIVATIVES

(75) Inventors: Peer Kirsch, Kanagawa (JP); Alexander Hahn, Gross-Gerau (DE); Eike Poetsch, Muehltal (DE); Werner Binder, Dieburg (DE); Volker Meyer, Gross-Zimmern (DE)

(73) Assignee: Merck Patent GmbH, Darmstadt (DE)

( * ) Notice: Subject to any disclaimer, the term of this patent is extended or adjusted under 35 U.S.C. 154(b) by 619 days.

(21) Appl. No.: 10/536,803

(22) PCT Filed: Nov. 17, 2003

(86) PCT No.: PCT/EP03/12812

§ 371 (c)(1),
(2), (4) Date: May 27, 2005

(87) PCT Pub. No.: WO2004/048357

PCT Pub. Date: Jun. 10, 2004

(65) Prior Publication Data

US 2006/0058527 A1    Mar. 16, 2006

(30) Foreign Application Priority Data

Nov. 27, 2002    (DE) ................. 102 55 312

(51) Int. Cl.
*C07D 315/00* (2006.01)
(52) U.S. Cl. ..................... 549/427; 549/425
(58) Field of Classification Search ................. 549/427, 549/428
See application file for complete search history.

(56) References Cited

U.S. PATENT DOCUMENTS

| 4,755,323 | A | * | 7/1988 | Eidenschink et al. ... | 252/299.61 |
| 4,818,431 | A | * | 4/1989 | Eidenschink et al. ... | 252/299.61 |
| 5,443,755 | A | | 8/1995 | Namekawa et al. | |
| 5,595,684 | A | | 1/1997 | Namekawa et al. | |
| 5,958,290 | A | | 9/1999 | Finkenzeller et al. | |
| 6,558,758 | B1 | * | 5/2003 | Yanai et al. ................. | 428/1.1 |
| 6,902,777 | B2 | * | 6/2005 | Hirschmann et al. ......... | 428/1.1 |

FOREIGN PATENT DOCUMENTS

| DE | 41 32 006 | 4/1993 |
| EP | 0 594 861 | 5/1994 |
| EP | 0 684 246 | 11/1995 |
| EP | 0 700 983 | 3/1996 |

* cited by examiner

*Primary Examiner*—Janet L. Andres
*Assistant Examiner*—Raymond Covington
(74) *Attorney, Agent, or Firm*—Millen, White, Zelano & Branigan, P.C.

(57) ABSTRACT

The invention relates to tetrahydropyran derivatives of the general formula I and to processes for the preparation thereof.

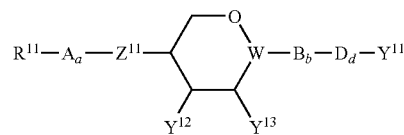

20 Claims, No Drawings

TETRAHYDROPYRAN DERIVATIVES

The invention relates to tetrahydropyran derivatives and to processes for the preparation thereof.

Tetrahydropyran derivatives play an important role in chemistry and pharmacy, inter alia as constituents of natural and synthetic aroma substances, in medicaments and in liquid-crystalline materials. However, preparative access to tetrahydropyrans is currently limited and is usually restricted to derivatisation of carbohydrates containing pyranose ring units.

One object of the present invention is therefore to provide tetrahydropyran derivatives which are suitable as synthones for the construction of complex molecules containing tetrahydropyran units.

This object is achieved by the provision of compounds of the general formula I

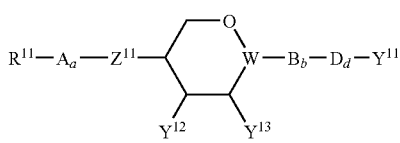

in which $R^{11}$ denotes H, F, Cl, Br, I, CN, aryl, heterocyclyl or a halogenated or unsubstituted alkyl radical having 1 to 15 carbon atoms, where, in addition, one or more $CH_2$ groups in this radical may each be replaced, independently of one another, by —C≡C—, —CH=CH—, —O—, —CO—, —CO—O— or —O—CO— in such a way that O atoms are not linked directly to one another;

A stands for

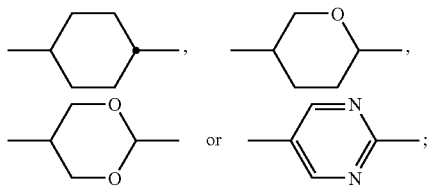

a is 0, 1 or 2, where A can adopt identical or different meanings if a is 2;

$Z^{11}$ represents a single bond, —$CH_2$—$CH_2$—, —$CF_2$—$CF_2$—, —$CF_2$—$CH_2$—, —$CH_2$—$CF_2$—, —$CH_2$—O—, —O—$CH_2$—, —$CF_2$—O— or —O—$CF_2$—;

W denotes >CH— or >C=;

B and D, independently of one another, stand for

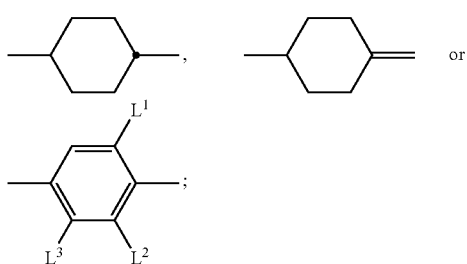

b and d, independently of one another, are 0 or 1;

$Y^{11}$ denotes =O, =C($SR^{12}$)($SR^{13}$), =$CF_2$, —H, —F, —Cl, —Br, —I, —CN, —OH, —SH, —CO—$R^{14}$, —$OSO_2R^{15}$, —C(=$S^+R^{12}$)(—$SR^{13}$)$X^-$, —B($OR^{16}$)($OR^{17}$), —$BF_3^-$$Cat^+$, —Si($OR^{18}$)($OR^{19}$)($OR^{20}$) or alkyl, where alkyl denotes a halogenated or unsubstituted alkyl radical having 1 to 15 C atoms, in which, in addition, one or more $CH_2$ groups may each be replaced, independently of one another, by —C≡C—, —CH=CH—, —O—, —CO—, —CO—O— or —O—CO— in such a way that O atoms are not linked directly to one another;

$Y^{12}$ and $Y^{13}$, independently of one another, denote H or alkyl, where alkyl denotes a halogenated or unsubstituted alkyl radical having 1 to 15 C atoms, in which, in addition, one or more $CH_2$ groups may each be replaced, independently of one another, by —C≡C—, —CH=CH—, —O—, —CO—, —CO—O— or —O—CO— in such a way that O atoms are not linked directly to one another;

$L^1$, $L^2$ and $L^3$, independently of one another, denote H or F;

$R^{12}$ and $R^{13}$, independently of one another, denote an unbranched or branched alkyl radical having 1 to 15 carbon atoms or together form a —$(CH_2)_p$— unit, where p=2, 3, 4, 5 or 6, where one, two or three of these $CH_2$ groups may be substituted by at least one unbranched or branched alkyl radical having 1 to 8 carbon atoms;

$R^{14}$ denotes OH, O-aryl, O-aralkyl, O-alkyl, Cl, Br, aryl, aralkyl or alkyl;

$R^{15}$ denotes aryl, aralkyl or a halogenated or unsubstituted alkyl radical having 1 to 15 carbon atoms, where, in addition, one or more $CH_2$ groups in this alkyl radical may each be replaced, independently of one another, by —C≡C—, —CH=CH—, —O—, —CO—, —CO—O— or —O—CO— in such a way that O atoms are not linked directly to one another;

$R^{16}$ and $R^{17}$ denote H or an unbranched or branched alkyl radical having 1 to 15 carbon atoms or together form a —$(CH_2)_p$— unit, where p=2, 3, 4, 5 or 6, where one, two or three of these $CH_2$ groups may be substituted by at least one unbranched or branched alkyl radical having 1 to 8 carbon atoms;

$R^{18}$, $R^{19}$ and $R^{20}$, independently of one another, denote an unbranched or branched alkyl radical having 1 to 15 carbon atoms;

$Cat^+$ is an alkali metal cation or a quaternary ammonium cation; and $X^-$ is a weakly coordinating anion; with the proviso that W denotes >CH— if b+d≠0;

that $Y^{11}$ does not denote =O, =C($SR^{12}$)($SR^{13}$) or =$CF_2$ if $Y^{11}$ is connected to B or

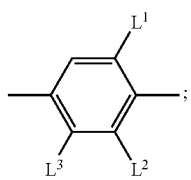

D= that $Y^{11}$ denotes —H, —I, —OH, —SH, —$CO_2R^{14}$, —$OSO_2R^{15}$, —C(=$S^+R^{12}$)($SR^{13}$)$X^-$, —B($OR^{16}$)($OR^{17}$), —$BF_3^-Cat^+$, —Si($OR^{18}$)($OR^{19}$)($OR^{20}$) or alkyl (where alkyl denotes a halogenated or unsubstituted alkyl radical having 1 to 15 C atoms, in which one or more $CH_2$ groups have each been replaced, independently of one another, by —C≡C—, —CH=CH—, —O—, —CO—, —CO—O— or —O—CO— in such a way that O atoms are not linked directly to one another and alkyl does not stand for alkoxy) if W is connected directly to

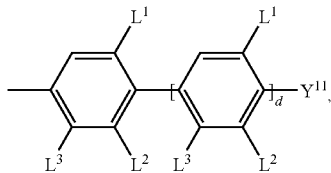

where d is 0 or 1; and that B does not stand for

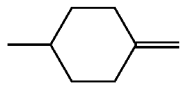

if d=1.

The compounds according to the invention are useful as intermediate compounds for the preparation of more complex molecules which contain a tetrahydropyran unit as molecule constituent and are used, for example, as aroma substance, medicament and a component of, in particular, liquid-crystalline mixtures for use in electro-optical devices.

The term "alkyl"—unless defined otherwise elsewhere in this description or in the claims—encompasses saturated and unsaturated acyclic (aliphatic) hydrocarbon radicals, each of which may be unsubstituted or substituted by halogen.

"alkyl" encompasses, inter alia, straight-chain and branched saturated alkyl groups (alkanyls) having 1-15, preferably 1, 2, 3, 4, 5, 6 or 7 carbon atoms, in particular the straight-chain groups methyl, ethyl, propyl, butyl, pentyl, hexyl and heptyl, furthermore octyl, nonyl, decyl, undecyl, dodecyl, tridecyl, tetradecyl and pentadecyl. Groups having 2-5 carbon atoms are generally preferred. The term "alkyl" furthermore encompasses hydrocarbon radicals which are mono- or polyhalogenated by fluorine, chlorine, bromine and/or iodine, such as, for example, —$CF_3$, —$CHF_2$ or —$CH_2F$. Preferred branched alkyl radicals are isopropyl, 2-butyl, isobutyl, tert-butyl, 2-methylbutyl, isopentyl, 2-methylpentyl, 3-methylpentyl, 2-ethylhexyl and 2-propylpentyl.

In its most general meaning, the term "alkyl" also encompasses, inter alia, alkenyl radicals, i.e. at least one $CH_2$ group of the alkyl radical has been replaced by —CH=CH—, where the —CH=CH— group may also be in the terminal position as H—CH=CH— or each of the CH units may also be substituted by halogen (such as, for example, in —CF=CH— or —CF=CF—); and alkynyl radicals, i.e. at least one $CH_2$ group of the alkyl radical has been replaced by —C≡C—, where the —C≡C— group may also be in the terminal position as H—C≡C—. Alkenyl and alkynyl radicals have, independently of one another, 2 to 15 carbon atoms, preferably 2, 3, 4, 5, 6 or 7 carbon atoms. The alkenyl radicals can be in the form of E and/or Z isomers, with the respective E isomer generally being preferred. Preferred alkenyl groups are $H_2C$=CH—, $CH_3$—CH=CH— and $C_2H_5$—CH=CH—, a preferred alkynyl group is $H_3C$—C≡C—.

For the purposes of this invention, the term "alkyl" furthermore also encompasses those radicals in which one or more $CH_2$ groups have been replaced by O in such a way that the oxygen atoms are not bonded directly to one another, i.e. alkoxy and oxaalkyl radicals which have 1 to 15, preferably 1, 2, 3, 4, 5, 6 or 7 carbon atoms and are particularly preferably unbranched. Preferred alkoxy radicals are methoxy, ethoxy, propoxy, butoxy, pentoxy, hexoxy, heptoxy and (per)fluorinated alkoxy radicals, such as —$OCH_2F$, —$OCHCF_2$, —$OCF_3$, —$OCH_2CF_3$ or —$OCF_2CF_3$, furthermore octoxy, nonoxy, decoxy, undecoxy, dodecoxy, tridecoxy, tetradecoxy. Preferred branched alkoxy radicals are isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy. Preferred oxaalkyl radicals are 2-oxapropyl (=methoxymethyl), 2-oxabutyl (=ethoxymethyl), 3-oxabutyl, 2-, 3- or 4-oxapentyl, 2-, 3-, 4- or 5-oxahexyl, 2-, 3-, 4-, 5- or 6-oxaheptyl; furthermore, inter alia, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

The term "alkyl" also encompasses radicals in which one $CH_2$ group has been replaced by —CO—. These radicals are preferably straight-chain and have 2 to 7 carbon atoms.

For the purposes of the present invention, the term "alkyl" additionally also encompasses radicals in which one $CH_2$ group has been replaced by —O— and one has been replaced by —CO—, where these are preferably adjacent. These thus include an acyloxy group —CO—O— and an oxycarbonyl group —O—CO—. These are preferably straight-chain and have 2 to 7 carbon atoms. Accordingly, they denote in particular acetoxy, propionyloxy, butyryloxy, pentanoyloxy, hexanoyloxy, acetoxymethyl, propionyloxymethyl, butyryloxymethyl, pentanoyloxymethyl, hexanoyloxymethyl, 2-acetoxyethyl, 2-propionyloxyethyl, 2-butyryloxyethyl, 2-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

For the purposes of the present invention, "alkyl" furthermore also encompasses a radical in which one $CH_2$ group has been replaced by unsubstituted or substituted —CH=CH— and an adjacent $CH_2$ group has been replaced by CO or CO—O or O—CO, where this radical can be straight-chain or branched. It is preferably straight-chain and has 4 to 12 carbon atoms. Accordingly, it denotes in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6 methacryloyloxyhexyl, 7-methacryloyloxyheptyl, 8-methacryloyloxyoctyl, 9-methacryloyloxynonyl.

For the purposes of this invention, the term "alkyl" also encompasses radicals in which two or more $CH_2$ groups have been replaced by —O— and/or —CO—O—, where these can be straight-chain or branched. These radicals are preferably branched and have 3 to 12 carbon atoms. Accordingly, they denote in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2- bis(ethoxycarbonyl)ethyl, 3,3-bis(ethoxycarbonyl)propyl, 4,4-bis(ethoxycarbonyl)butyl, 5,5-bis(ethoxycarbonyl) hexyl.

For the purposes of the present invention, the term "aryl"—unless defined otherwise elsewhere in the description or in the claims—encompasses aromatic hydrocarbon radicals, preferably having 6 to 18 carbon atoms, which are optionally monosubstituted or polysubstituted by identical or different F, Cl, Br, I, CN, OH, SH, O-alkyl, S-alkyl, COOH, COO-alkyl, amino, $NO_2$ or alkyl. "Aryl" preferably stands for a phenyl or naphthyl radical, in each case optionally substituted in the 4-position by alkyl, or a biphenyl radical.

For the purposes of the present invention, the term "heterocyclyl"—unless defined otherwise elsewhere in the description or in the claims—encompasses heterocyclic saturated and unsaturated, inter alia also heteroaromatic radicals in which at least one ring atom is a heteroatom selected from the group consisting of O, S and N. The heterocyclyl radical is optionally monosubstituted or polysubstituted by identical or different F, Cl, Br, I, CN, OH, SH, O-alkyl, S-alkyl, COOH, COO-alkyl, amino, $NO_2$, aryl or alkyl. Heterocyclyl is preferably dioxanyl, furanyl, thienyl, pyranyl, pyrrolidinyl, piperidinyl, morpholinyl and pyrimidinyl. The linking of the heterocyclyl radical to an atom, a chain, a ring or another molecule constituent can generally take place via any ring atom.

For the purposes of the present invention, the term "aralkyl"—unless defined otherwise elsewhere in the description or in the claims—encompasses hydrocarbon radicals having an aryl constituent and an alkyl bridge, such as, for example, benzyl or phenethyl (phenyl-$CH_2$—$CH_2$—). In particular, the aryl constituent may be substituted as defined above for "aryl". "Aralkyl" is particularly preferably benzyl and phenethyl. For the purposes of this invention, an "O-aralkyl" radical is an aryl-alkyl-O radical, i.e. the linking to a further atom, a further chain, a further ring or another molecule constituent takes place via an alkyl-oxygen bridge. An example of O-aralkyl is —Obenzyl (—O—$CH_2$-phenyl).

In connection with the present invention, halogen denotes fluorine, chlorine, bromine and/or iodine.

In the compounds of the formula I according to the invention, A denotes 1,4-cyclohexylene, 2,5-tetrahydropyranylene, 2,5-dioxanylene or 2,5-pyrimidinylene, where the saturated rings are preferably trans-linked. Depending on the meaning of a—i.e. 0, 1 or 2—A in the compounds of the formula I according to the invention is not present (if a=0) or is present once (if a=1) or twice (if a=2). If a=2, A can have the same meaning twice, for example can be

or can be different rings, for example

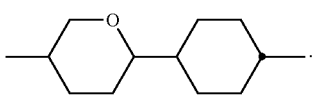

In a preferred embodiment of the present invention, A in the formula I denotes

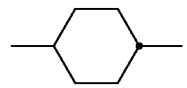

A preferably denotes 1,4-cyclohexylene if $Z^{11}$ is a single bond or —$CF_2O$— or —$OCF_2$—. In a furether preferred embodiment of the invention, the compounds according to the invention contain no ring A, i.e. a=0.

In the compounds of the formula I according to the invention, $Z^{11}$ represents a single bond, —$CH_2$—$CH_2$—, —$CF_2$—$CF_2$—, —$CF_2$—$CH_2$—, —$CH_2$—$CF_2$—, —$CH_2$—O—, —O—$CH_2$—, —$CF_2$—O— or —O—$CF_2$—. It is preferred for $Z^{11}$ to represent a single bond or —$CF_2O$— or —$OCF_2$—. In particular, $Z^{11}$ stands for a single bond, so that A or $R^{11}$ (if a=0) is bonded directly to the central tetrahydropyran ring.

In the compounds of the formula I according to the invention, $R^{11}$ denotes H, F, Cl, Br, I, CN, aryl, heterocyclyl or an alkyl radical as defined above. $R^{11}$ is preferably an unbranched halogenated or unsubstituted alkanyl radical having 1 to 7 carbon atoms, in particular $CF_3$—, $CF_3$—$CF_2$—, $CF_3$—$CH_2$—, methyl, ethyl, propyl, butyl, pentyl, hexyl or heptyl.

The substituents of the central tetrahydropyran ring, $Y^{12}$ and $Y^{13}$, independently of one another, denote H or an alkyl as defined above. It is preferred for both substituents $Y^{12}$ and $Y^{13}$ to denote hydrogen, so that the central tetrahydropyran ring of the compounds according to the invention is 2,5-difunctionalised.

In the compounds of the formula I according to the invention, W stands for >CH— or is >C=. If W stands for >CH—, W is linked to the radical B or D or to $Y^{11}$ via a single bond. If W stands for >C=, b=d=0, and W is linked to $Y^{11}$ via a double bond.

The rings B and D in the compounds of the formula I according to the invention denote, independently of one another,

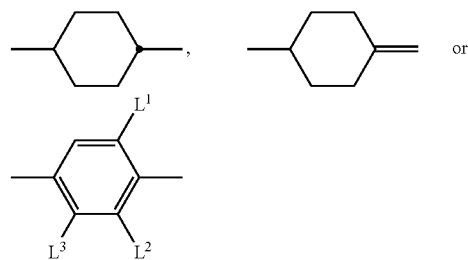

where B does not denote

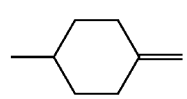

if a ring D is also present, i.e. if b=d=1. Depending on the meaning of the indices b and d, which can each be, independently of one another, 0 or 1, the compounds of the formula I are preferably in the form of

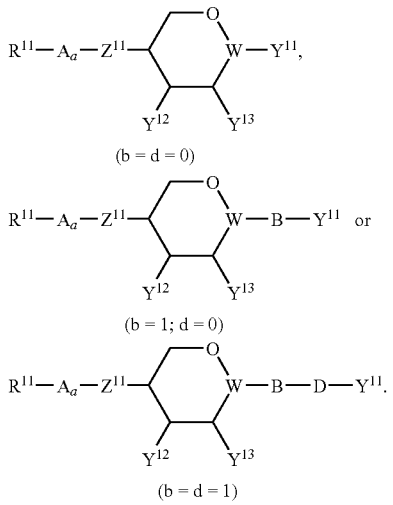

(b = d = 0)

(b = 1; d = 0)

(b = d = 1)

If b=d=0, W preferably stands for >C=. If one of the rings B and D is a 1,4-phenylene ring which is optionally substituted by $L^1$, $L^2$ and/or $L^3$, it is preferred for $L^1$, $L^2$ and $L^3$ all to stand for hydrogen or for $L^1$ and $L^2$ to denote fluorine and $L^3$ to denote hydrogen.

In the compounds of the formula I according to the invention, $Y^{11}$ denotes =O, =C($SR^{12}$)($SR^{13}$) or =$CF_2$ if $Y^{11}$ is linked to W=>C= or is bonded to B or D=

If $Y^{11}$ stands for =C($SR^{12}$)($SR^{13}$), $R^{12}$ and $R^{13}$ denote, independently of one another, an unbranched or branched alkyl radical having 1 to 15 carbon atoms or together form a —$(CH_2)_p$— unit, where p=2, 3, 4, 5 or 6, where one, two or three of these $CH_2$ groups may be substituted by at least one unbranched or branched alkyl radical having 1 to 8 carbon atoms. It is preferred for $R^{12}$ and $R^{13}$ either to have the same meaning, i.e., for example, for both to stand for ethyl or n-propyl, or together form a —$(CH_2)_p$— unit as defined above, which is optionally substituted by alkyl radicals. $R^{12}$ and $R^{13}$ together particularly preferably stand for —$CH_2$—$CH_2$—$CH_2$— or —$CH_2$—$C(CH_3)_2$—$CH_2$—.

In the compounds of the formula I according to the invention, $Y^{11}$ stands for —H, —F, —Cl, —Br, —I, —CN, —OH, —SH, —CO—$R^{14}$, —$OSO_2R^{15}$, —C(=$S^+R^{12}$)(—$SR^{13}$)$X^-$, —B($OR^{16}$)($OR^{17}$), —$BF_3$—$Cat^+$, —Si($OR^{18}$)($OR^{19}$)($OR^{20}$) or an alkyl as defined above if W stands for >CH— or $Y^{11}$ is linked to B or D via a single bond.

$R^{12}$ and $R^{13}$ here denote, independently of one another, an unbranched or branched alkyl radical having 1 to 15 carbon atoms or together form a —$(CH_2)_p$—unit, where p=2, 3, 4, 5 or 6, where one, two or three of these $CH_2$ groups may be substituted by at least one unbranched or branched alkyl radical having 1 to 8 carbon atoms; $R^{12}$ and $R^{13}$ preferably either have the same meaning, i.e. are, for example, both ethyl or n-propyl, or together form a —$(CH_2)_p$— unit as defined above, which is optionally substituted by alkyl radicals. $R^{12}$ and $R^{13}$ together particularly preferably stand for —$CH_2$—$CH_2$—$CH_2$— or —$CH_2$—$C(CH_3)_2$—$CH_2$—.

$R^{14}$ denotes aryl, aralkyl, alkyl, OH, Cl, Br, O-aryl, O-aralkyl or O-alkyl (alkoxy), where the aryl, aralkyl and alkyl radicals are as defined above. $R^{14}$ is preferably OH or an unsubstituted straight-chain or branched saturated O-alkyl radical (O-alkanyl or alkoxy respectively) having 1 to 4 carbon atoms, in particular O-methyl, O-ethyl, O-(n-propyl), O-(isopropyl), O-(n-butyl) or O-(tert-butyl), or an O-aralkyl radical, in particular O-benzyl.

$R^{15}$ denotes aryl, aralkyl or a halogenated or unsubstituted alkyl radical having 1 to 15 carbon atoms, where, in addition, one or more $CH_2$ groups in this alkyl radical may each be replaced, independently of one another, by —C≡C—, —CH=CH—, —O—, —CO—O— or —O—CO— in such a way that O atoms are not linked directly to one another. $R^{15}$ is preferably aryl, in particular phenyl or 4-tolyl, or a saturated unsubstituted or (per)halogenated alkyl radical having 1 to 4 carbon atoms, in particular methyl, ethyl, n-propyl, n-butyl, tert-butyl, $CF_3$, n-$C_4F_9$ and t-$C_4F_9$.

$R^{16}$ and $R^{17}$ denote H or an unbranched or branched alkyl radical having 1 to 15 carbon atoms or together form a —$(CH_2)_p$— unit, where p=2, 3, 4, 5 or 6, where one, two or three of these $CH_2$ groups may be substituted by at least one unbranched or branched alkyl radical having 1 to 8 carbon atoms. They are preferably both H or both a saturated alkyl radical having 1 to 4 carbon atoms, in particular methyl, ethyl, n-propyl, isopropyl, n-butyl or tert-butyl, or together form a cyclic bridge, in particular —$CH_2$—$CH_2$—$CH_2$— or —$CH_2$—$C(CH_3)_2$—$CH_2$—.

$R^{18}$, $R^{19}$ and $R^{20}$, independently of one another, denote an unbranched or branched alkyl radical having 1 to 15 carbon atoms. They are preferably, independently of one another, saturated alkyl radicals having 1 to 4 carbon atoms, in particular methyl, ethyl, n-propyl, isopropyl, n-butyl or tert-butyl. In particularly preferred embodiments, $R^{18}$, $R^{19}$ and $R^{20}$ are all simultaneously methyl.

$Cat^+$ is an alkali metal cation, i.e. $Li^+$, $Na^+$, $K^+$, $Rb^+$ or $Cs^+$, or a quaternary ammonium cation, for example $NH_4^+$ or $N(alkyl)_4^+$, where alkyl is as defined above and the four alkyl radicals are identical or different. $Cat^+$ is preferably $Na^+$, $K^+$, $NH_4^+$ or a tetramethyl- or tetra-n-butylammonium cation $X^-$ is a weakly coordinating anion, i.e. a ligand which binds only relatively weakly to the sulfur cation. $X^-$ is preferably $BF_4^-$, $CF_3SO_3^-$, $C_4F_9SO_3^-$, $PF_6^-$, $SbF_6^-$ or $AsF_6^-$.

Of the substituents $Y^{11}$ which are linked via a single bond, particular preference is given to —H, —F, —Cl, —Br, —I, —OH, —$CO_2H$ (i.e. —CO—$R^{14}$ where $R^{14}$=OH), —C(=$S^+R^{12}$)(—$SR^{13}$)$X^-$ and B($OR^{16}$)($OR^{17}$), in particular —Br, —OH, —C(=$S^+R^{12}$)(—$SR^{13}$)$X^-$, —B($OR^{16}$)($OR^{17}$), —$BF_3Cat^+$ and —Si($OR^{18}$)($OR^{19}$)($OR^{20}$). If W is bonded directly to

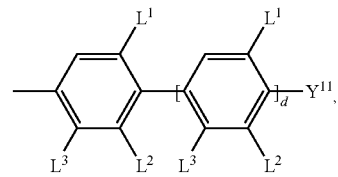

where d is 0 or 1, $Y^{11}$ is preferably —H, —I, —OH, —SH, —$CO_2R^{14}$, —$OSO_2R^{15}$, —$C(=S^+R^{12})(SR^{13})X^-$, —$B(OR^{16})(OR^{17})$, —$BF_3Cat^+$, —$Si(OR^{18})(OR^{19})(OR^{20})$ or alkyl, where alkyl denotes a halogenated or unsubstituted alkyl radical having 1 to 15 C atoms, in which one or more $CH_2$ groups have each been replaced, independently of one another, by —C≡C—, —CH=CH—, —O—, —CO—, —CO—O— or —O—CO— in such a way that O atoms are not linked directly to one another and alkyl is not alkoxy.

Preferred compounds of the formula I according to the invention are those which are reproduced by one of the following formulae:

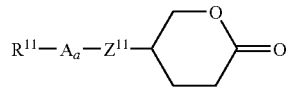
I1

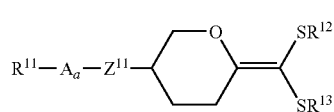
I2

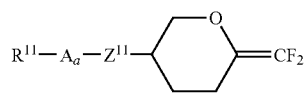
I3

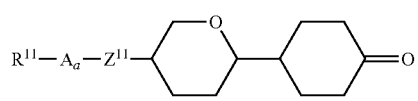
I4

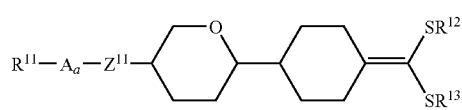
I5

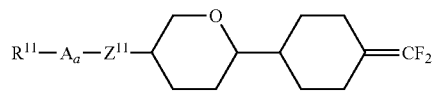
I6

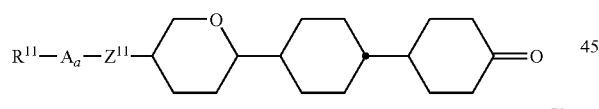
I7

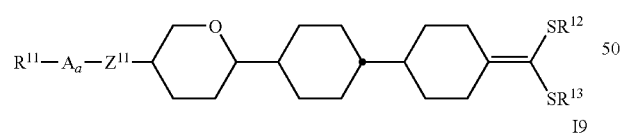
I8

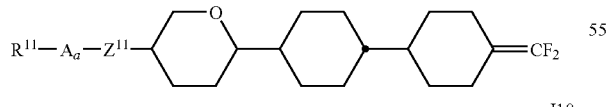
I9

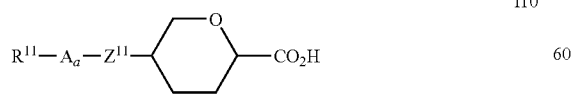
I10

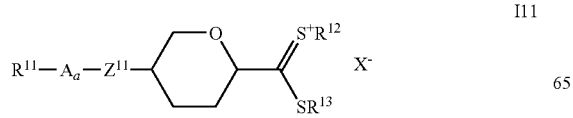
I11

-continued

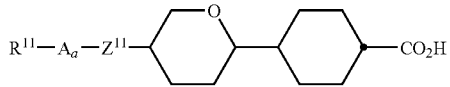
I12

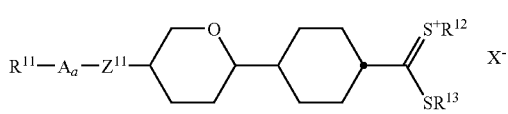
I13

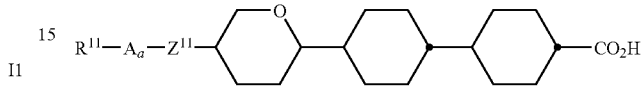
I14

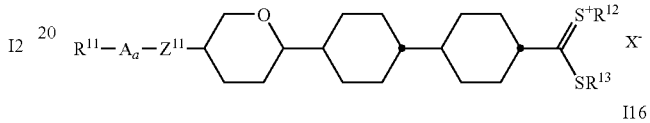
I15

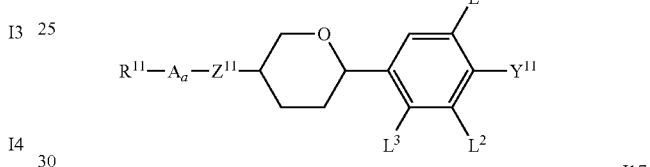
I16

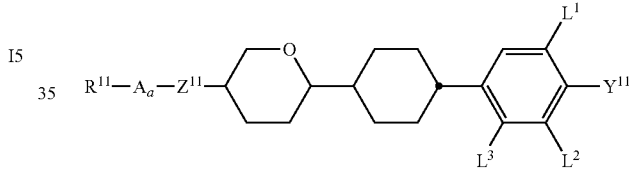
I17

In these formulae, $R^{11}$, A, a, $Z^{11}$, $Y^{11}$, $L^1$, $L^2$, $L^3$, $R^{12}$, $R^{13}$ and $X^-$ have the meanings indicated above.

Particularly preferred compounds of the formula I are:

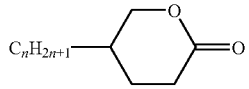
I1a

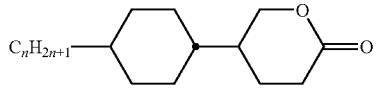
I1b

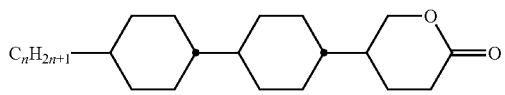
I1c

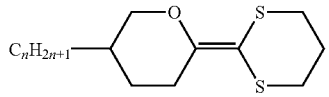
I2a

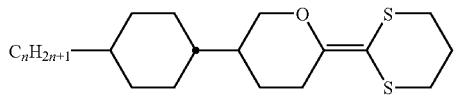
I2b

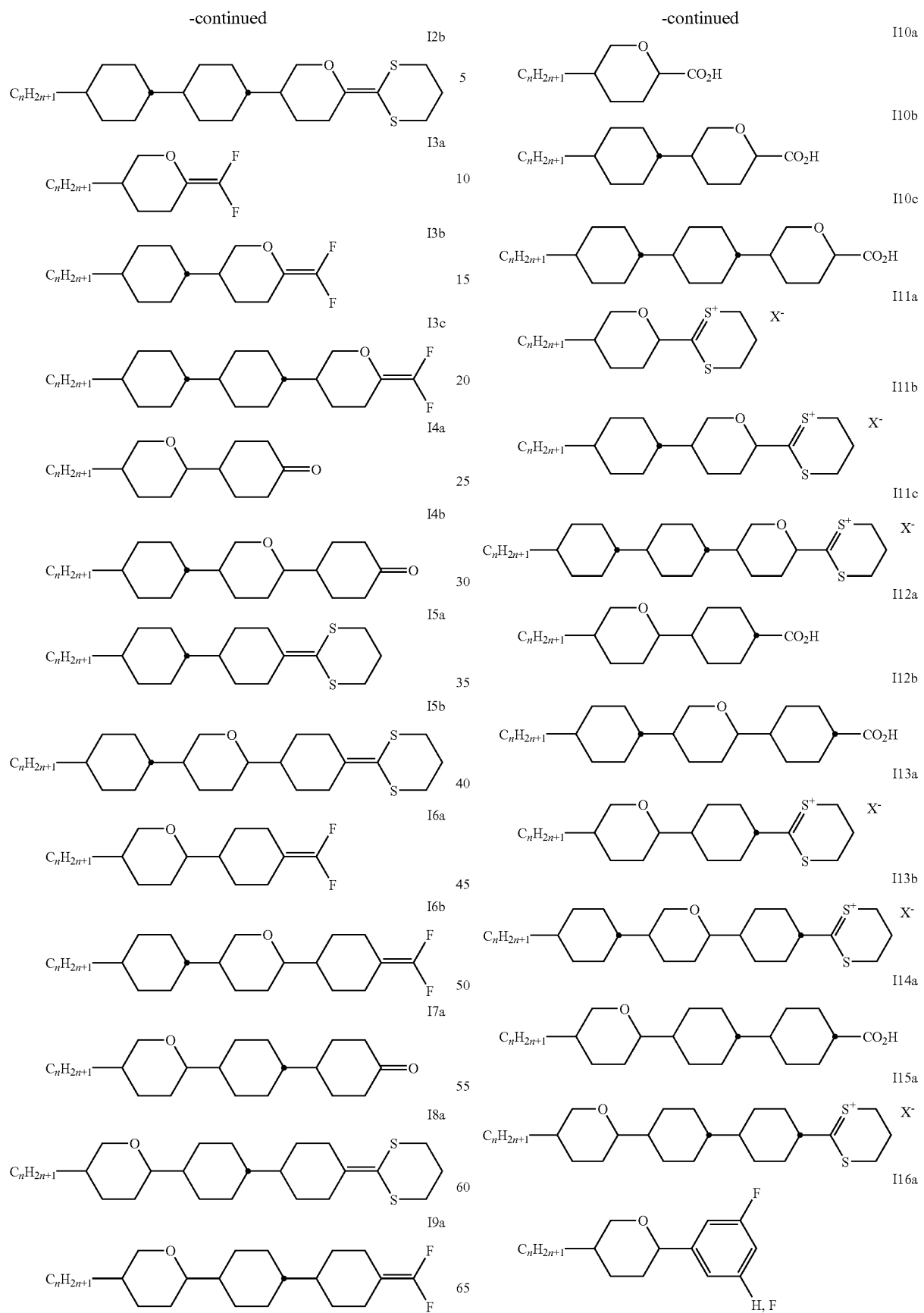

-continued

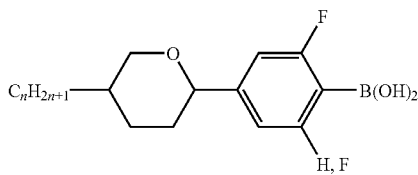
I16b

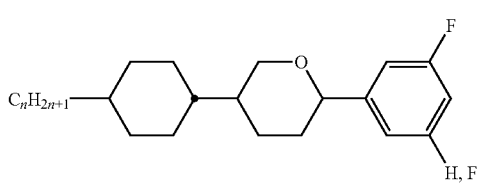
I16c

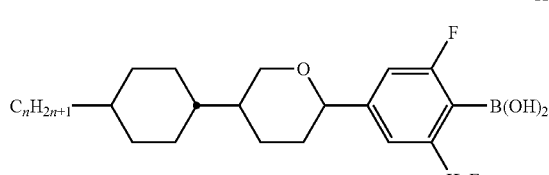
I16d

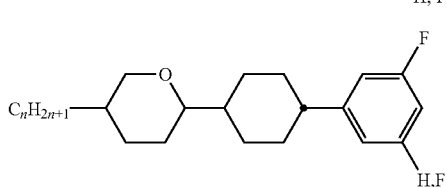
I17a

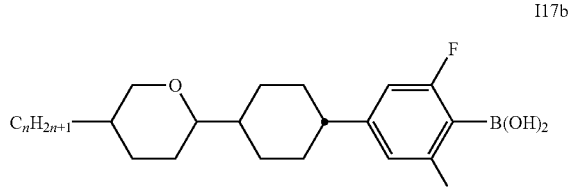
I17b

In these formulae, n is an integer from 1 to 7, in particular 1, 2, 3, 4 or 5. $C_nH_{2n+1}$ is branched or preferably straight-chain.

The compounds of the formula I according to the invention can be prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

Compounds of the formula I according to the invention are preferably prepared by one of the following processes according to the invention:

A first process gives access to compounds of the formula IA

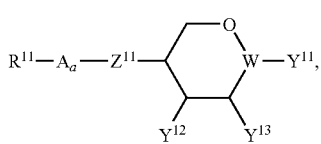
IA in which

W denotes >C=;

$Y^{11}$ denotes =O, =C($SR^{12}$)($SR^{13}$) or =CF$_2$; and $R^{11}$, A, a, $Z^{11}$, $Y^{12}$, $Y^{13}$, $R^{12}$ and $R^{13}$ are as defined above for the formula I;

where the process is characterised in that a compound of the formula II

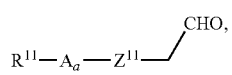
II in which $R^{11}$, A, a and $Z^{11}$ are as defined above for the formula IA, is reacted in a reaction step (A1)

(A1) in the presence of a base with a compound of the formula III

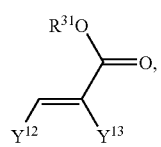
III in which $Y^{12}$ and $Y^{13}$ are as defined above for the formula IA, and $R^{31}$ denotes an alkyl radical having 1 to 15 carbon atoms, to give a compound of the formula IV

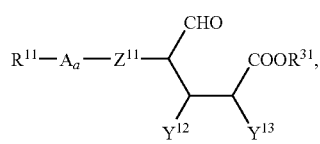
IV in which $R^{11}$, A, a, $Z^{11}$, $Y^{12}$ and $Y^{13}$ are as defined above for the formula IA, and $R^{31}$ is as defined above for the formula III; and subsequently, in a reaction step (A2), (A2) the compound of the formula IV is converted into the compound IA1

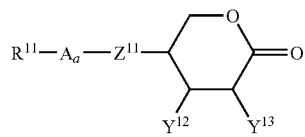
IA1 with reduction of the aldehyde function and with lactone formation; and optionally, in a reaction step (A3), (A3) the compound of the formula IA1 is converted into the compound IA2

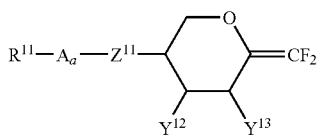

IA2 by reaction with $CF_2Br_2$ in the presence of $P(N(R^{21})_2)_3$, $P(N(R^{21})_2)_2(OR^{22})$ or $P(N(R^{21})_2)(OR^{22})_2$, where $R^{21}$ and $R^{22}$, independently of one another, is an alkyl radical having 1 to 15 carbon atoms, in particular denotes methyl or ethyl;
or optionally, in a reaction step (A3'),
(A3') the compound of the formula IA1 is converted into the compound IA3

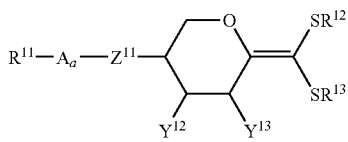

IA3 by reaction with $CHG(SR^{12})(SR^{13})$, in which G denotes $P(OCH_2R^{23})_3$, where $R^{23}$ is a perfluorinated alkyl radical having 1 to 5 carbon atoms, in particular $CF_3$, $CF_2CF_3$ or $C_4F_9$, or $Si(CH_3)_3$ or $Si(CH_2CH_3)_3$, and $R^{12}$ and $R^{13}$ are as defined above for the formula IA, in the presence of a strong base.

The compounds of the formulae II and III are known from the literature or readily accessible using synthetic methods known from the prior art, or modifications thereof. Reaction step (A1) is generally carried out at temperatures above room temperature and preferably at the reflux temperature of the solvent. Suitable solvents are all solvents which dissolve the reactants to an extent which is adequate for the progress of the reaction; preference is given to the use of acetonitrile or propionitrile. Suitable bases are reagents which form an intermediate enamine with the compound of the formula II, in particular dialkylamines and trialkylsilyldialkylamines, for example trimethylsilyldiethylamine, which then reacts to completion with the compound of the formula II. The reduction of the aldehyde function of the compound of the formula IV to a hydroxyl function in step (A2) is carried out using selectively acting reducing agents which are known from the prior art, for example sodium borohydride. The lactonisation to give compound IA1 which completes reaction step (A2) can be effected, for example, using catalytic amounts of an acid, for example toluenesulfonic acid.

Starting from the lactone of the formula IA1 according to the invention, further compounds of the formulae IA2 or IA3 according to the invention can, if desired, be prepared in reaction steps (A3) and (A3') respectively: The conversion of compound IA1 into compound IA2 is carried out with the aid of $CF_2Br_2$ in the presence of $P(N(R^{21})_2)_3$, $P(N(R^{21})_2)_2(OR^{22})$ or $P(N(R^{21})_2)(OR^{22})_2$, where $R^{21}$ and $R^{22}$, independently of one another, is an alkyl radical having 1 to 15 carbon atoms, in particular methyl or ethyl, in a suitable solvent, for example THF and/or dioxane, preferably at room temperature. Reaction step (A3') is carried out in the presence of a strong base, preferably an organolithium base, such as n-butyllithium, or potassium tert-butoxide, preferably in ethereal solvents, such as THF, at temperatures between −80° C. and room temperature.

A further process according to the invention gives access to compounds of the formula IB

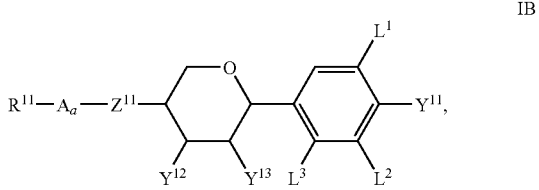

IB in which
$Y^{11}$ denotes —H, —F, —Cl, —Br, —I, —CN, —OH or —$B(OR^{16})(OR^{17})$, and $R^{11}$, A, a, $Z^{11}$, $Y^{12}$, $Y^{13}$, $L^1$, $L^2$, $L^3$, $R^{16}$, $R^{17}$ are as defined above for the formula I, and which is characterised in that, in a reaction step (B1),
(B1) a compound of the formula IA1

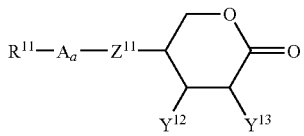

IA1 in which $R^{11}$, A, a, $Z^{11}$, $Y^{12}$ and $Y^{13}$ are as defined above for the formula IB, is reacted with a compound of the formula V

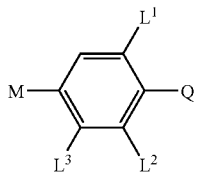

V in which $L^1$, $L^2$ and $L^3$ are as defined above for the formula IB, M denotes Li, Cl—Mg, Br—Mg or I—Mg, and Q denotes H, F, Cl, Br, I or CN, with formation of the compound of the formula IB1

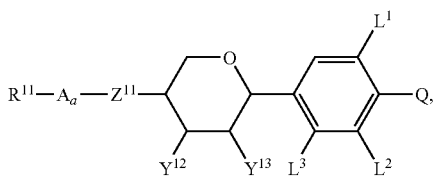

IB1 in which $R^{11}$, A, a, $Z^{11}$, $Y^{12}$, $Y^3$, $L^1$, $L^2$ and $L^3$ are as defined for the formula IB, and Q is as defined for the formula V;
and optionally, in a reaction step (B2),
(B2) the compound of the formula IB1 in which Q denotes Br is reacted with $B(OR^{16})(OR^{17})(OR^{24})$, where $R^{16}$, $R^{17}$ and $R^{24}$ are an unbranched or branched alkyl radical having 1 to 15 carbon atoms, or with $HB(OR^{16})(OR^{17})$, where $R^{16}$ and $R^{17}$ denote an unbranched or branched alkyl radical having 1 to 15 carbon atoms or together form a —$(CH_2)_p$— unit, where p=2, 3, 4, 5 or 6, where one, two or three of these CH$_2$ groups may be substituted by at least one unbranched or branched alkyl radical having 1 to 8 carbon atoms, in the presence of an alkyllithium base, to give the compound of the formula IB2

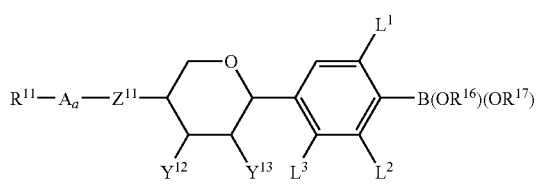

IB2 and optionally, in a reaction step (B3),
(B3) the compound IB2 is converted into the compound IB3

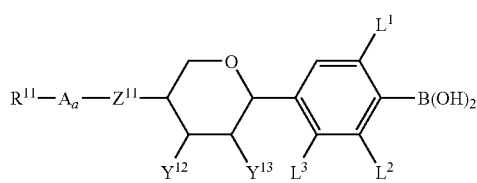

IB3 by reaction with an aqueous acid; and/or optionally, in a reaction step (B4), (B4) the compound IB2 or the compound IB3 is converted into the compound IB4

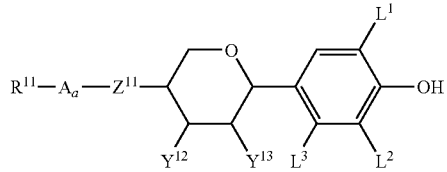

IB4 by reaction with hydrogen peroxide in alkaline or acidic solution, for example in aqueous sodium hydroxide solution or acetic acid.

The compound of the formula V used in reaction step (B1) is accessible in a manner known per se from the corresponding halogenated compound by metal-halogen exchange by means of an organolithium base or by the Grignard method, for example by reaction with magnesium. M in the formula V is preferably lithium. Reaction step (B1) is preferably carried out in an ethereal solvent, for example diethyl ether, at temperatures between −80° C. and room temperature. The reduction of the hydroxyl function formed as an intermediate after addition of compound V onto the carbonyl function of the compound of the formula IA1 to give the compound of the formula IB1 is carried out using a suitable reducing agent, for example trialkylsilane and boron trifluoride etherate.

The alkyllithium base used in optional reaction step (B2) is preferably methyllithium or n-butyllithium, preferably in an ethereal solvent, for example THF, or in hexane. After lithium-halogen exchange has been carried out (preferably at temperatures between −80° C. and room temperature), the product is reacted with a suitable boric acid derivative, for example trialkyl borate, with formation of the compound of the formula IB2. If desired, the corresponding boric acid of the formula IB3 can be liberated therefrom in reaction step (B3) using aqueous acid, for example 2N hydrochloric acid. In optional reaction step (B4)—starting from IB2 or IB3—the corresponding phenol of the formula IB4 can be prepared using hydrogen peroxide in alkaline solution, for example 30% H$_2$O$_2$ in sodium hydroxide solution, or acidic solution, for example in acetic acid.

A further process according to the invention gives access to compounds of the formula IC according to the invention:

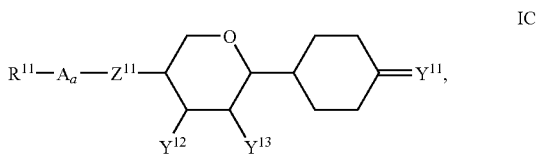

IC in which
Y$^{11}$ denotes =O, =C(SR$^{12}$)(SR$^{13}$) or =CF$_2$, and
R$^{11}$, A, a, Z$^{11}$, Y$^{12}$, Y$^{13}$, R$^{12}$ and R$^{13}$ are as defined above for the formula I, and which is characterised in that, in a reaction step (C1),
(C1) the compound of the formula IB4

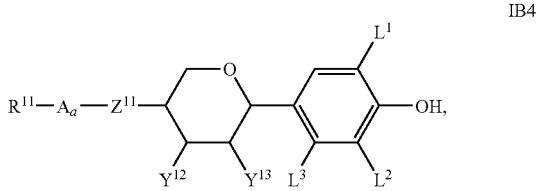

IB4 in which R$^{11}$, A, a, Z$^{11}$, Y$^{12}$ and Y$^{13}$ are as defined above for the formula IC, and L$^1$, L$^2$ and L$^3$ denote H, is converted into the compound IC1

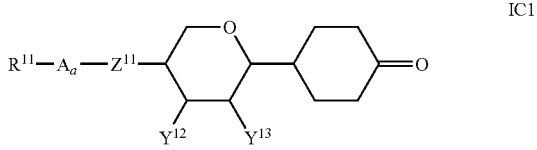

IC1

(i.e. into the compound IC in which Yak is =O) using hydrogen in the presence of a transition-metal catalyst;
and optionally, in a reaction step (C2),
(C2) the compound IC1 is converted into the compound IC2

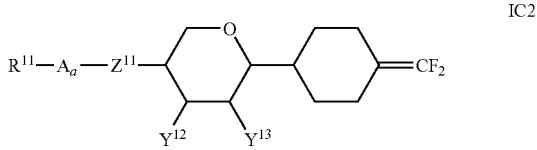

IC2

(i.e. the compound IC in which Y$^{11}$ is =CF$_2$) by reaction with CF$_2$Br$_2$ in the presence of P(N(R$^{21}$)$_2$)$_3$, P(N(R$^{21}$)$_2$)$_2$(OR$^{22}$) or P(N(R$^{21}$)$_2$)(OR$^{22}$)$_2$, where R$^{21}$ and R$^{22}$, independently of one another, are an alkyl radical having 1 to 15 carbon atoms and in particular denote methyl or ethyl;
or optionally, in a reaction step (C2'),
(C2') the compound of the formula IC1 is converted into the compound IC3

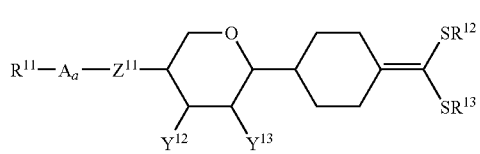

(i.e. the compound IC in which $Y^{11}$ is $=C(SR^{12})(SR^{13})$) by reaction with $CHG(SR^{12})(SR^{13})$, in which G denotes $P(OCH_2R^{23})_3$, where $R^{23}$ is a perfluorinated alkyl radical having 1 to 5 carbon atoms, in particular $CF_3$, $CF_2CF_3$ or $C_4F_9$, or $Si(CH_3)_3$ or $Si(CH_2CH_3)_3$, and $R^{12}$ and $R^{13}$ are as defined above for the formula IC, in the presence of a strong base.

The transition-metal catalyst used in reaction step (C1) is a catalyst usually used for hydrogenation reactions, for example palladium on carbon; the reaction conditions which are usual for this type of hydrogenation are selected (see, for example, J. March: Advanced Organic Chemistry; John Wiley & Sons, New York, inter alia, 3rd Edn., 1985, pp. 700-702, 5-11). The further optional reaction steps (C2) and (C2') are essentially carried out under the same conditions as reaction steps (A3) and (A3') above.

A further process according to the invention is used for the preparation of compounds of the formula ID according to the invention:

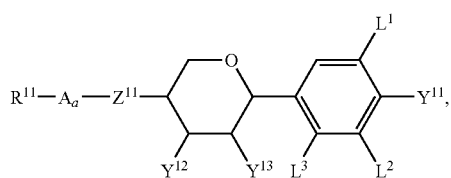

in which
$Y^{11}$ denotes $—CO_2H$ or $—C(=S^+R^{12})(—SR^{13})X^-$, and $R^{11}$, A, a, $Z^{11}$, $Y^{12}$, $Y^{13}$, $R^{12}$, $R^{13}$, $L^1$, $L^2$, $L^3$ and X are as defined above for the formula I,
and which is characterised in that, in a reaction step (D1),
(D1) a compound of the formula IB1

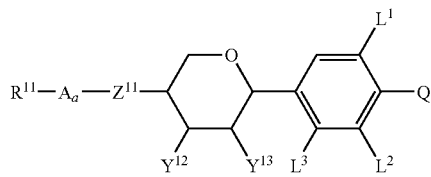

in which $R^{11}$, A, a, $Z^{11}$, $Y^{12}$, $Y^{13}$, $L^1$, $L^2$ and $L^3$ are as defined for the formula ID, and Q denotes H or Br, is reacted firstly with an organometallic base and then with $CO_2$ to give the compound ID1

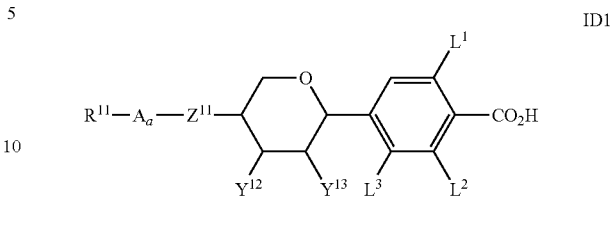

in which $R^{11}$, A, a, $Z^{11}$, $Y^{12}$, $Y^{13}$, $L^1$, $L^2$ and $L^3$ are as defined for the formula ID;
and optionally, in a reaction step (D2),
(D2) the compound ID1 is converted into the compound ID2

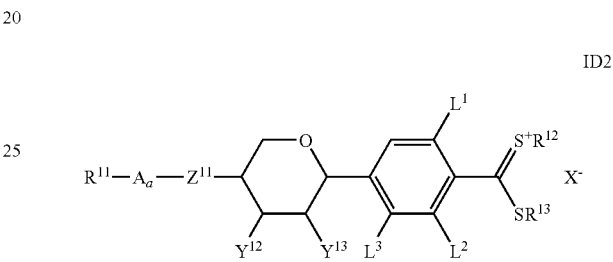

in the presence of an acid HX using $HSR^{12}$ and $HSR^{13}$ or using $HSR^{12}R^{13}SH$.

The organometallic base used in reaction step (D1) is preferably an organolithium base, for example n-butyllithium in THF or hexane; the metallation is preferably carried out at temperatures between −40° C. and room temperature. The $CO_2$ used to scavenge the metallated compound formed as an intermediate can be introduced as gaseous carbon dioxide or preferably added in solid form as dry ice. Aqueous work-up gives the desired benzoic acid derivative ID1.

In optional reaction step (D2), the thiol reagent used is preferably a dithiol, for example 1,3-propanethiol or 2,2-dimethylpropane-1,3-dithiol, in the presence of an acid, for example toluenesulfonic acid.

A further process according to the invention gives access to further compounds of the formula IE according to the invention:

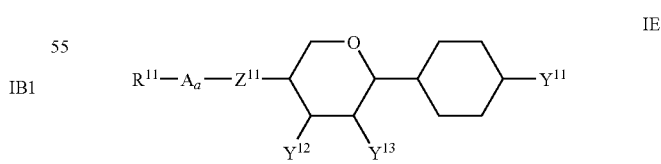

in which
$Y^{11}$ denotes $—CO_2H$ or $—C(=S^+R^{12})(—SR^{13})X^-$, and $R^{11}$, A, a, $Z^{11}$, $Y^{12}$, $Y^{13}$, $R^{12}$ and $R^{13}$ and X are as defined above for the formula I,
and which is characterised in that, in a reaction step (E1), (E1) the compound of the formula ID1

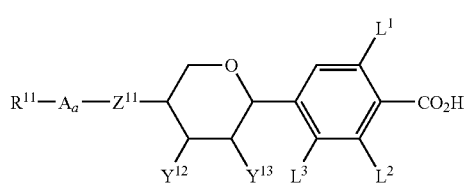

in which $R^{11}$, A, a, $Z^{11}$, $Y^{12}$ and $Y^{13}$ are as defined above for the formula IE, and $L^1$, $L^2$ and $L^3$ denote H, is converted into the compound IE1

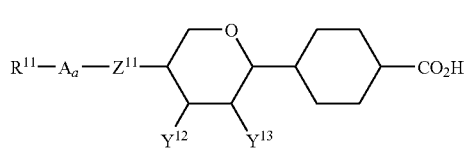

using hydrogen in the presence of a transition-metal catalyst; and optionally, in a reaction step (E2),
(E2) the compound of the formula IE1 is converted into the compound IE2

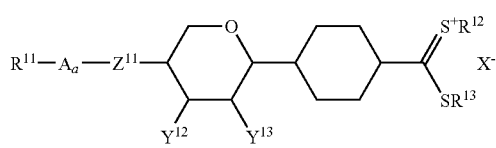

in the presence of an acid HX using $HSR^{12}$ and $HSR^{13}$ or using $HSR^{12}R^{13}SH$.

For details of the performance of reaction steps (E1) and (E2), reference is made to reaction steps (C1) and (D2) respectively.

Persons skilled in the art will recognise that further compounds according to the invention can be synthesised by appropriate adaptation or repetition of certain reaction steps of the processes according to the invention. They will furthermore be capable, with the aid of their expert knowledge, to carry out exact adjustment of reaction parameters, such as the precise amount of reactants, the reaction time and temperature and the choice and quantity of the reagents and solvent, in accordance with the necessities of the particular reaction.

If the compounds according to the invention can occur in the form of optical isomers, for example in the form of enantiomers and/or diastereomers—if they carry, for example, a chiral radical $R^{11}$—these compounds are also covered by the scope of the description and claims. These chiral compounds can be in the form of a mixture of the isomers, preferably in the form of a racemate, or alternatively in isomerically pure form. The isomerically pure or isomerically enriched compounds according to the invention are accessible in a manner known per se by conventional resolution methods, for example chromatography on chiral phases or fractional crystallisation, optionally in the presence of chiral reagents, or by specific asymmetric synthesis.

The compounds according to the invention can be employed as starting compounds for complex molecules containing a tetrahydropyran ring. Thus, for example, starting from compounds of the formulae I2, I3, I5, I6, I8, I9, I11, I13 or I15, the corresponding compounds in which the terminal radical ($Y^{11}$) has been replaced by a —$CF_2$O-aryl group can be obtained analogously to processes known per se from the literature. Tetrahydropyran derivatives which have been functionalised in this way have mesogenic properties.

The present invention is illustrated further by the following examples, without it being intended for these to restrict the scope of the invention.

EXAMPLES

The starting compounds, reagents and solvents employed in the examples are—unless stated otherwise—commercially available. The products were characterised by conventional analytical methods, inter alia GC, HPLC, mass spectrometry, $^1$H- and $^{19}$F-NMR spectroscopy, DSC and polarisation microscopy.

The preparation of the compounds of Examples 1 to 7 followed the following synthetic scheme 1:

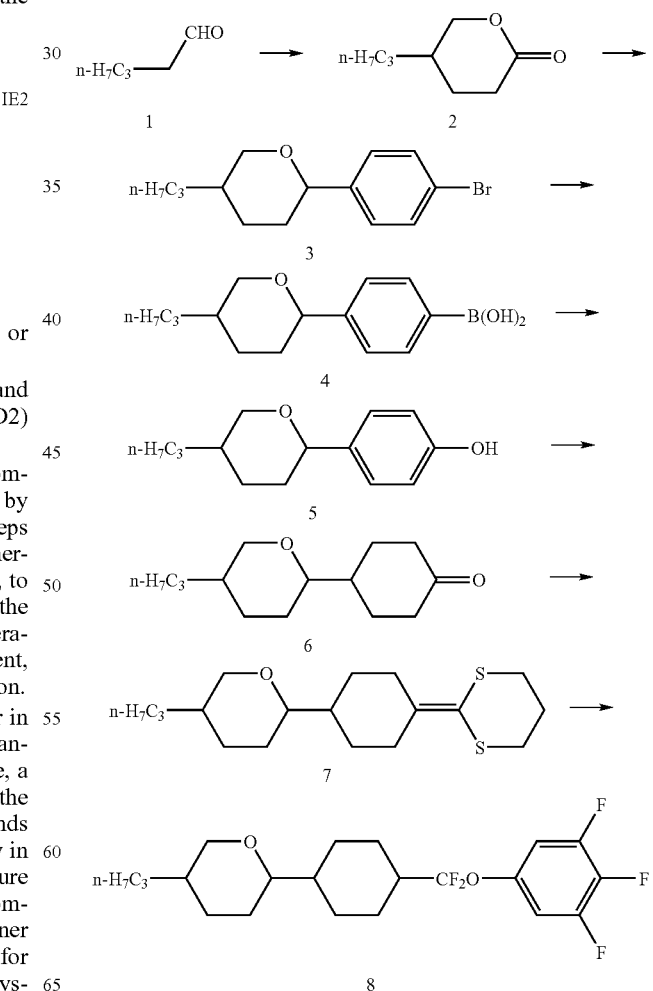

Example 1

Compound 2

A mixture of 500 mmol of pent-1-al (1), 700 mmol of methyl acrylate, 50 mmol of trimethylsilyldiethylamine and 300 ml of acetonitrile was heated at the boil for 18 h. The mixture was evaporated under reduced pressure, with acetonitrile and silanes being removed. 2.5 mol of glacial acetic acid were then added, and the mixture was stirred at 50° C. for 18 h. The mixture was neutralised by addition of 2N NaOH and diluted with 3 l of sat. NaCl solution. The organic phase was separated off, washed with sat. NaCl solution and dried over $Na_2SO_4$. 1 l of isopropanol and subsequently 250 mmol of sodium borohydride were added, and the mixture was stirred for 18 h. The mixture was subjected to aqueous work-up, and the organic phase was washed twice with sat. NaCl solution and dried using $Na_2SO_4$. The crude alcohol was boiled with 1 l of toluene and 1 g of toluenesulfonic acid on a water separator until the reaction was complete. The solution was washed until neutral and subsequently purified by distillation. Yield of the lactone (2): 35% of a liquid with an intense woodruff-like odour. Boiling point: 137-138° C. (19 mbar).

Example 2

Compound 3

207 mmol of n-butyllithium (15% in hexane) were added dropwise at −50° C. to a solution of 207 mmol of 1,4-dibromobenzene in 250 ml of diethyl ether. A solution of 170 mmol of 2 in 50 ml of diethyl ether was then added dropwise at the same temperature, and the mixture was stirred for a further 30 min, allowed to warm to 0° C. and subjected to aqueous work-up. The crude product (51 g) was dissolved in 400 ml of dichloromethane, and 400 mmol of triethylsilane were added at −75° C. 400 mmol of boron trifluoride etherate were added dropwise, during which the temperature was kept below −70° C. The temperature was then allowed to rise to −10° C., and the mixture was hydrolysed using saturated sodium hydrogencarbonate solution and subjected to aqueous work-up. The crude product comprised the trans/cis isomers in a ratio of 9:1. The product was recrystallised from pentane at −20° C.; yield of compound 3: 30.6 g, 61%. Melting point: 43° C.

Example 3

Compound 4

73 mmol of 3 were dissolved in 200 ml of THF and cooled to −70° C. Firstly 73 mmol of n-butyllithium (15% in hexane) were added dropwise, followed by 73 mmol of trimethyl borate in 50 ml of THF. The mixture was allowed to warm to −20° C., adjusted to pH 2 by addition of 2N HCl and subjected to aqueous work-up. The crude product was digested using hot heptane and crystallised at 0° C. Yield of compound 4: 13.1 g, 72%.

Example 4

Compound 5

A mixture of 60 mmol of 4, 300 ml of toluene, 120 mmol of NaOH, 50 ml of water and 30 ml of 30% $H_2O_2$ was stirred at 45° C. for 2 h. The mixture was adjusted to pH 2 using 10% HCl and subjected to aqueous work-up. The crude product was recrystallised from heptane. Yield of compound 5: 7.1 g, 52%.

Example 5

Compound 6

22 mmol of 5 were hydrogenated at 5 bar and 130° C. for 27.5 h in 100 ml of xylene in the presence of 1.5 g of 5% Pd/C catalyst. The mixture was subjected to conventional work-up. Yield of compound 6: 65%, colourless oil.

Example 6

Compound 7

17 mmol of n-butyllithium (15% in hexane) were added at −70° C. to a solution of 17 mmol of 2-trimethylsilyl-1,3-dithiane in 75 ml of THF. The mixture was allowed to come to 0° C. over the course of 4 h, then re-cooled to −70° C., 17 mmol of 6 in 25 ml of THF were added dropwise, and the mixture was allowed to come to room temperature, stirred for a further 18 h and subjected to aqueous work-up. The crude product was crystallised from heptane. Yield of compound 7: 40%, colourless crystals.

Example 7

Compound 8

6.27 mmol of trifluoromethanesulfonic acid were added dropwise at −20° C. to a solution of 6.12 mmol of 7 in 50 ml of dichloromethane. The mixture was allowed to come to room temperature for 30 min and was then cooled to −70° C. Then, firstly a solution 9.1 mmol of 3,4,5-trifluorophenol and 10.1 mmol of triethylamine in 20 ml of dichloromethane and, 5 min later, 31 mmol of triethylamine tris(hydrofluoride) were added. After a further five minutes, a suspension of 31.5 mmol of DBH (1,3-dibromo-5,5-dimethylhydantoin) was added in small portions, and the mixture was stirred at −70° C. for a further one hour. The reaction mixture was allowed to come to −10° C. and was poured into 400 ml of ice-cold NaOH. The mixture was subjected to aqueous work-up, and the crude product was purified by chromatography on silica gel (heptane/toluene 3:2) and crystallisation from pentane at −70° C. Yield of compound 8: 42%, colourless crystals. Melting point: 35° C. Clearing point: 66.3° C.

The invention claimed is:

1. A compound of the general formula I

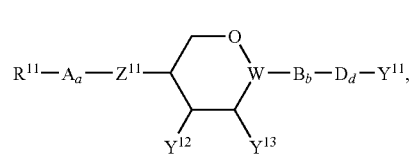

in which $R^{11}$ denotes H, F, Cl, Br, I, CN, aryl, heterocyclyl or a halgenated or unsubstituted alkyl radical having 1 to 15 carbon atoms, in which one or more $CH_2$ groups are optionally replaced, independently of one another, by —C≡C—, —CH=CH—, —O—, —CO—, —CO—O— or —O—CO— in such a way that O atoms are not linked directly to one another;

A stands for

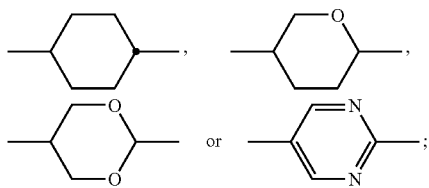

a is 0, 1 or 2;
$Z^{11}$ represents a single bond —CH$_2$—CH$_2$—, —CF$_2$—CF$_2$—, —CF$_2$—CH$_2$—, —CH$_2$—CF$_2$—, —CH$_2$—O—, —O—CH$_2$—, —CF$_2$—O— or —O—CF$_2$—;
W denotes >CH— or >C=;
B and D, independently of one another, stand for

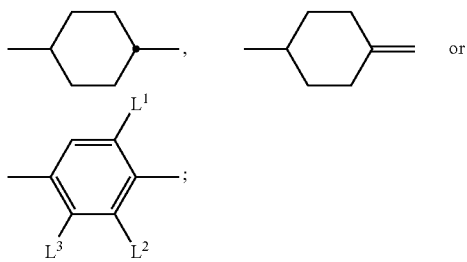

b and d, independently of one another, are 0 or 1;
$Y^{11}$ denotes =O, =C(SR$^{12}$)(SR$^{13}$), =CF$_2$, —H, —F, —Cl, —Br, —I, —CN, —OH, —SH, —CO—R$^{14}$, —OSO$_2$R$^{15}$, —C(=S$^+$R$^{12}$)(—SR$^{13}$)X$^-$, —B(OR$^{16}$)(OR$^{17}$), —BF$_3^-$Cat$^+$, —Si(OR$^{18}$)(OR$^{19}$)(OR$^{20}$) or alkyl, where alkyl denotes a halogenated or unsubstituted alkyl radical having 1 to 15 C atoms, in which, one or more CH$_2$ groups are optionally replaced, independently of one another, by —C≡C—, —CH=CH—, —O—, —CO—, —CO—O— or —O—CO— in such a way that O atoms are not linked directly to one another;
$Y^{12}$ and $Y^{13}$, independently of one another, denote H or alkyl, where alkyl denotes a halogenated or unsubstituted alkyl radical having 1 to 15 C atoms, in which, one or more CH$_2$ groups are optionally replaced, independently of one another, by —C≡C—, —CH=CH—, —O—, —CO—, —CO—O— or —O—CO— in such a way that O atoms are not linked directly to one another;
$L^1$, $L^2$ and $L^3$, independently of one another, denote H or F;
$R^{12}$ and $R^{13}$, independently of one another, denote an unbranched or branched alkyl radical having 1 to 15 carbon atoms or together form a —(CH$_2$)$_p$— unit, where p=2, 3, 4, 5 or 6, where one, two or three of these CH$_2$ groups are optionally substituted by at least one unbranched or branched alkyl radical having 1 to 8 carbon atoms;
$R^{14}$ denotes OH, O-aryl, O-aralkyl, O-alkyl, Cl, Br, aryl, aralkyl or alkyl;
$R^{15}$ denotes aryl, aralkyl or a halogenated or unsubstituted alkyl radical having 1 to 15 carbon atoms, in which alkyl radical one or more CH$_2$ groups are optionally replaced, independently of one another, by —C≡C—, —CH=CH—, —O—, —CO—, —CO—O— or —O—CO— in such a way that O atoms are not linked directly to one another;

$R^{16}$ and $R^{17}$ denote H or an unbranched or branched alkyl radical having 1 to 15 carbon atoms or together form a —(CH$_2$)$_p$— unit, where p=2, 3, 4, 5 or 6, where one, two or three of these CH$_2$ groups are optionally substituted by at least one unbranched or branched alkyl radical having 1 to 8 carbon atoms;

$R^{18}$, $R^{19}$ and $R^{20}$, independently of one another, denote an unbranched or branched alkyl radical having 1 to 15 carbon atoms;
Cat$^+$ is an alkali metal cation or a quaternary ammonium cation; and
X$^-$ is a weakly coordinating anion;
with the proviso
that W denotes >CH— if b+d≠0;
that $Y^{11}$ does not denote =O, =C(SR$^{12}$)(SR$^{13}$) or =CF$_2$ if $Y^{11}$ is connected to B
or D=

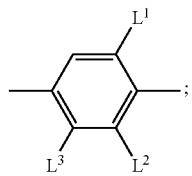

that $Y^{11}$ denotes —H, —I, —SH, —CO$_2$R$^{14}$, —OSO$_2$R$^{15}$, —C(=S$^+$R$^{12}$)(SR$^{13}$)X$^-$, —B(OR$^{16}$)(OR$^{17}$), —BF$_3^-$Cat$^+$, —Si(OR$^{18}$)(OR$^{19}$)(OR$^{20}$) or alkyl, where alkyl denotes a halogenated or unsubstituted alkyl radical having 1 to 15 C atoms, in which one or more CH$_2$ groups have each been replaced, independently of one another, by —C≡C—, —CH=CH—, —O—, —CO—, —CO—O— or —O—CO— in such a way that O atoms are not linked directly to one another and alkyl does not stand for alkoxy, if W is connected directly to

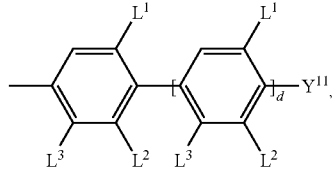

where
d is 0 or 1;
that B does not stand for

if d=1; and
that A can adopt identical or different meanings if a is 2.

2. A compound according to claim 1, wherein
A stands for

3. A compound according to claim 1, wherein
a is 0.
4. A compound according to claim 1, wherein
$Y^{12}$ and $Y^{13}$ denote H.
5. A compound according to claim 1, wherein
$Z^{11}$ represents a single bond, —$CF_2O$— or —$OCF_2$—.
6. A compound according to claim 1, wherein
$R^{11}$ denotes an unbranched halogenated or unsubstituted alkyl radial having 1 to 7 carbon atoms.
7. A compound according to claim 1, wherein
$Y^{11}$ denotes =O, =$C(SR^{12})(SR^{13})$ or =$CF_2$.
8. A compound according to claim 1, wherein
$Y^{11}$ denotes —H, —F, —Cl, —Br, —I, —OH, —$CO_2H$, —$C(=S^+R^{12})(-SR^{13})X^-$, —$B(OR^{16})(OR^{17})$, —$BF_3^- Cat^+$ or —$Si(OR^{18})(OR^{19})(OR^{20})$.
9. A compound according to claim 1, wherein
$X^-$ denotes $BF_4^-$, $CF_3SO_3^-$, $C_4F_9SO_3^-$, $PF_6^-$, $SbF_6^-$ or $AsF_6^-$.
10. A compound according to claim 1, wherein
b is 0 and d is 0.
11. A compound according to claim 1, wherein
b is 1 and d is 0.
12. A compound according to claim 1, wherein
b is 1 and d is 1.
13. A process for preparing compound of claim 1, which is a compound of formula IA

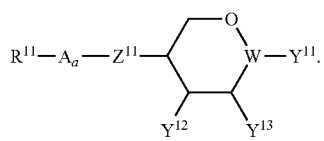

in which
$R^{11}$ denotes H, F, Cl, Br, I, CN, aryl, heterocyclyl a alkyl;
A stands for

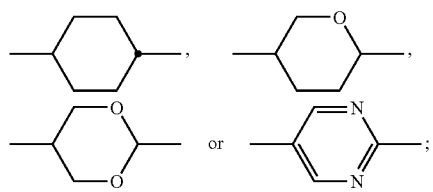

a is 0, 1 or 2, where A can adopt identical or different meanings if a is 2;
$Z^{11}$ represents a single bond, —$CH_2$—$CH_2$—, —$CF_2$—$CF_2$—, —$CF_2$—$CH_2$—, —$CH_2$—$CF_2$—, —$CH_2$—O—, —O—$CH_2$—, —$CF_2$—O— or —O—$CF_2$—;
W denotes >C=;
$Y^{11}$ denotes =O, =$C(SR^{12})(SR^{13})$ or =$CF_2$;
$Y^{12}$ and $Y^{13}$, independently of one another, denote H or alkyl; and $R^{12}$ and $R^{13}$, independently of one another, denote an unbranched or branched alkyl radical having 1 to 15 carbon atoms or together form a —$(CH_2)_p$—unit, where p=2, 3, 4, 5 or 6, where one, two or three of these $CH_2$ groups are optionally substituted by at least one unbranched or branched alkyl radical having 1 to 8 carbon atoms;

comprising reacting a compound of formula II

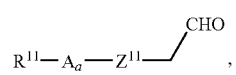

in which $R^{11}$, A, a and $Z^{11}$ are as defined above for the compound of formula IA,
in a reaction step (A1)
(A1) in the presence of a base with a compound of formula III

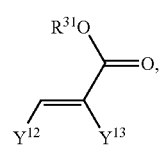

in which $Y^{12}$ and $Y^{13}$ are as defined above for the compound of formula IA, and $R^{31}$ denotes an alkyl radical having 1 to 15 carbon atoms, to give a confound of formula IV

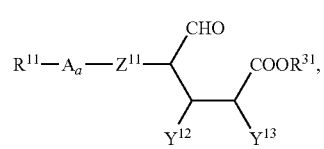

in which $R^{11}$, A, a, $Z^{11}$, $Y^{12}$ and $Y^{13}$ are as defined above for the compound of formula IA, and $R^{31}$ is as defined above for the compound of formula III; and subsequently converting in a reaction step (A2),
(A2) the compound of formula IV into a compound of formula IA1

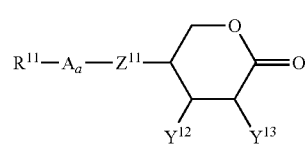

and optionally converting, in a reaction step (A3),
(A3) the compound of formula IA1 into a compound of formula IA2

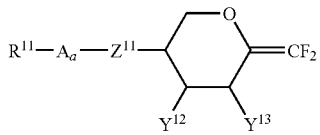

by reaction with $CF_2Br_2$ in the presence of $P(N(R^{21})_2)_3$, $P(N(R^{21})_2)_2(OR^{22})$ or $P(N(R^{21})_2)(OR^{22})$, where $R^{21}$ and $R^{22}$, independently of one another, denote an alkyl radical having 1 to 15 carbon atoms;

or optionally converting, in a reaction step (A3'), (A3') the compound of formula IA1 into a compound of formula IA3

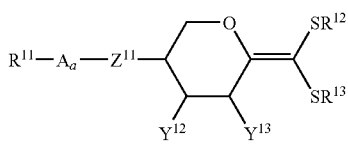

by reaction with $CHG(SR^{12})(SR^{13})$, in which G denotes $P(OCH_2R^{23})_3$, where $R^{23}$ is a perfluorinated alkyl radical having 1 to 5 carbon atoms, or $Si(CH_3)_3$ or $Si(CH_2CH_3)_3$, and $R^{12}$ and $R^{13}$ are as defined above for the compound of formula IA, in the presence of a strong base.

14. A process for preparing a compound of claim 1, which is a compound of formula IB

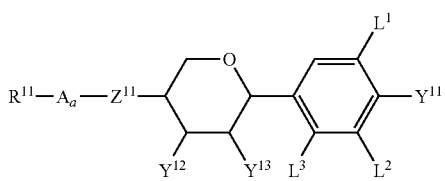

in which $R^{11}$ denotes H, F, Cl, Br, I, CN, aryl, heterocyclyl or alkyl;

A stands for

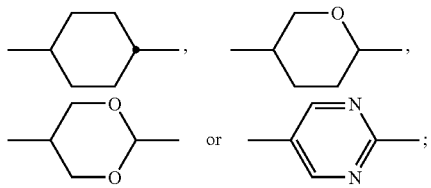

a is 0, 1 or 2, where A can adopt identical or different meanings if a is 2;

$Z^{11}$ represents a single bond, $-CH_2-CH_2-$, $-CF_2-CF_2-$, $-CF_2-CH_2-$, $-CH_2-CF_2-$, $-CH_2-O-$, $-O-CH_2-$, $-CF_2-O-$ or $-O-CF_2-$;

$Y^{11}$ denotes $-H$, $-F$, $-Cl$, $-Br$, $-I$, $-CN$, $-OH$ or $-B(OR^{16})(OR^{17})$;

$Y^{12}$ and $Y^{13}$, independently of one another, denote H or alkyl;

$L^1$, $L^2$ and $L^3$, independently of one another, denote H or F; and $R^{16}$ and $R^{17}$, independently of one another, denote H or an unbranched or branched alkyl radical having 1 to 15 carbon atoms or together form a $-(CH_2)-$ unit, where p=2, 3, 4, 5 or 6, where one, two or three of these $CH_2$ groups are optionally substituted by at least one unbranched or branched alkyl radical having 1 to 8 carbon atoms;

comprising reacting in a reaction step (B1), (B1) a compound of formula IA1

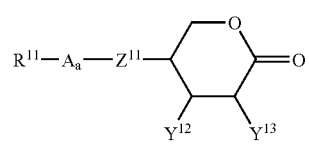

in which $R^{11}$, A, a, $Z^{11}$, $Y^{12}$ and $Y^{13}$ are as defined above for the compound of formula IB, with a compound of formula V

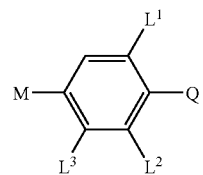

in which $L^1$, $L^2$ and $L^3$ are as defined above for the compound of formula IB, M denotes Li, Cl—Mg, Br—Mg or I—Mg, and Q denotes H, F, Cl, Br, I or CN, with formation of a compound of formula IB1

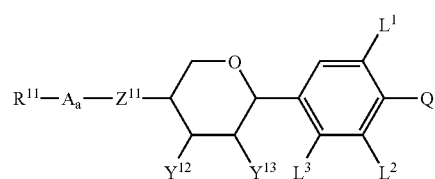

in which $R^{11}$, A, a, $Z^{11}$, $Y^{12}$, $Y^{13}$, $L^1$, $L^2$ and $L^3$ are as defined for the compound of formula IB, and Q is as defined for the formula V;

and optionally, in a reaction step (B2), (B2) the compound of the formula IB1 in which Q denotes Br with $B(OR^{16})(OR^{17})(OR^{24})$, where $R^{16}$, $R^{17}$ and $R^{24}$ are an unbranched or branched alkyl radical having 1 to 15 carbon atoms, or with $HB(OR^{16})(OR^{17})$, where $R^{16}$ and $R^{17}$ denote an unbranched or branched alkyl radical having 1 to 15 carbon atoms or together form a $-(CH_2)_p-$ unit, where p=2, 3, 4, 5 or 6, where one, two or three of these $CH_2$ groups are optionally substituted by at least one unbranched or branched alkyl radical having 1 to 8 carbon atoms, in the presence of an alkyllithium base, to give a compound of formula IB2

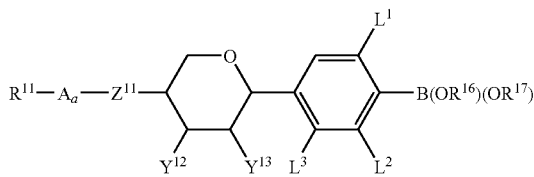

IB2 and optionally, in a reaction step (B3),
(B3) the compound IB2 into a compound of formula IB3

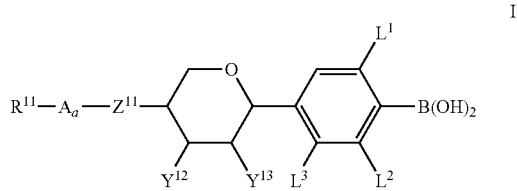

IB3 by reaction with an aqueous acid;
and/or optionally converting, in a reaction step (B4),
(B4) the compound of formula IB2 or the compound of compound IB3 into a compound of formula IB4

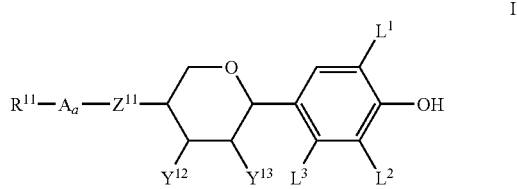

IB4 by reaction with hydrogen peroxide in alkaline or acidic solution.

15. A process for preparing a compound of claim 1, which is a compound of formula IC

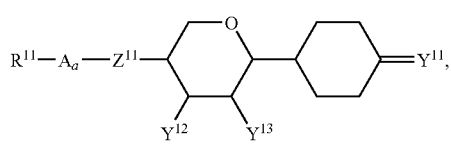

IC in which
$R^{11}$ denotes H, F, Cl, Br, I, CN, aryl, heterocyclyl or alkyl;
A stands for

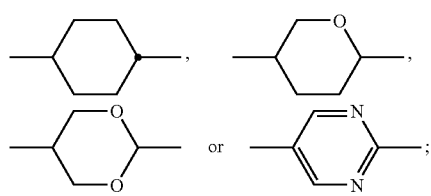

a is 0, 1 or 2, where A can adopt identical or different meanings if a is 2;

$Z^{11}$ represents a single bond, —$CH_2$—$CH_2$—, —$CF_2$—$CF_2$—, —$CF_2$—$CH_2$—, —$CH_2$—$CF_2$—, —$CH_2$—O—, —O—$CH_2$—, —$CF_2$—O— or —O—$CF_2$—;

$Y^{11}$ denotes =O, =$C(SR^{12})(SR^{13})$ or =$CF_2$;

$Y^{12}$ and $Y^{13}$, independently of one another, denote H or alkyl; and $R^{12}$ and $R^{13}$, independently of one another, denote an unbranched or branched alkyl radical having 1 to 15 carbon atoms or together form a —$(CH_2)_p$— unit, where p=2, 3, 4, 5 or 6, where one, two or three of these $CH_2$ groups are optionally substituted by at least one unbranched or branched alkyl radical having 1 to 8 carbon atoms;

comprising
converting in a reaction step (C1),
(C1) the compound of formula IB4

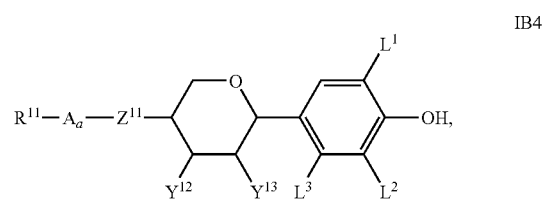

IB4 in which $R^{11}$, A, a, $Z^{11}$, $Y^{12}$ and $Y^{13}$ are as defined above for the compound of formula IC, and $L^1$, $L^2$ and $L^3$ denote H, into a compound of formula IC1

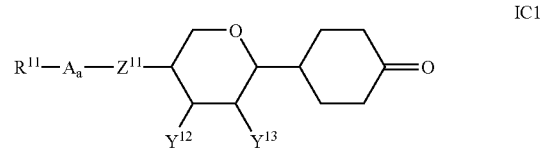

IC1 using hydrogen in the presence of a transition-metal catalyst;

and optionally converting, in a reaction step (C2),
(C2) the compound of formula IC1 into a compound of formula IC2

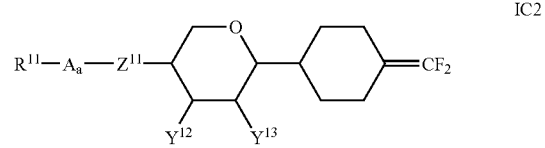

IC2 by reaction with $CF_2Br_2$ in the presence of $P(N(R^{21})_2)_3$, $P(N(R^{21})_2)_2(OR^{22})$ or $P(N(R^{21})_2)(OR^{22})_2$, where $R^{21}$ and $R^{22}$, independently of one another, are an alkyl radical having 1 to 15 carbon atoms;

or optionally, in a reaction step (C2'),
(C2') the compound of formula IC1 into a compound of formula IC3

IC3 by reaction with $CHG(SR^{12})(SR^{13})$, in which G denotes $P(OCH_2R^{23})_3$, where $R^{23}$ is a perfluorinated alkyl radical having 1 to 5 carbon atoms, or $Si(CH_3)_3$ or $Si(CH_2CH_3)_3$, and $R^{12}$ and $R^{13}$ are as defined above for the compound of formula IC, in the presence of a strong base.

16. A process for preparing a compound of claim 1, which is a compound of formula ID

ID in which $R^{11}$ denotes H, F, Cl, Br, I, CN, aryl, heterocyclyl or alkyl;

A stands for or a is 0, 1 or 2, where A can adopt identical or different meanings if a is 2;

$Z^{11}$ represents a single bond, $-CH_2-CH_2-$, $-CF_2-CF_2-$, $-CF_2-CH_2-$, $-CH_2-CF_2-$, $-CH_2-O-$, $-O-CH_2-$, $-CF_2-O-$ or $-O-CF_2-$;

$Y^{11}$ denotes $-CO_2H$ or $-C(=S^+R^{12})(-SR^{13})X^-$;

$Y^{12}$ and $Y^{13}$, independently of one another, denote H or alkyl;

$L^1$, $L^2$ and $L^3$, independently of one another, denote H or F;

$R^{12}$ and $R^{13}$, independently of one another, denote an unbranched or branched alkyl radical having 1 to 15 carbon atoms or together form a $-(CH_2)_p-$unit, where $p=2, 3, 4, 5$ or 6, where one, two or three of these $CH_2$ groups are optionally substituted by at least one unbranched or branched alkyl radical having 1 to 8 carbon atoms; and $X^-$ is a weakly coordinating anion;

comprising reacting, in a reaction step (D1), (D1) a compound of the formula IB1

IB1 in which $R^{11}$, A, a, $Z^{11}$, $Y^{12}$, $Y^{13}$, $L^1$, $L^2$ and $L^3$ are as defined for the compound of formula ID, and Q denotes H or Br, with an organometallic base and $CO_2$ to give a compound of formula ID1

ID1 in which $R^{11}$, A, a, $Z^{11}$, $Y^{12}$, $Y^{13}$, $L^1$, $L^2$ and $L^3$ are as defined for the compound of formula ID;

and optionally, in a reaction step (D2), (D2) the compound ID1 into a compound of formula ID2

ID2 in the presence of an acid HX using $HSR^{12}$ and $HSR^{13}$ or using $HSR^{12}R^{13}SH$.

17. A process for preparing a compound of claim 1, which is a compound of formula IE

IE in which $R^{11}$ denotes H, F, Cl, Br, I, CN, aryl, heterocyclyl or alkyl;

A stands for

,

-continued

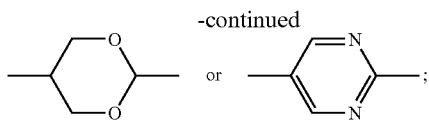

a is 0, 1 or 2, where A can adopt identical or different meanings if a is 2;

$Z^{11}$ represents a single bond, —$CH_2$—$CH_2$—, —$CF_2$—$CF_2$—, —$CF_2$—$CH_2$—, —$CH_2$—$CF_2$—, —$CH_2$—O—, —O—$CH_2$—, —$CF_2$—O— or —O—$CF_2$—;

$Y^{11}$ denotes —$CO_2H$ or —$C(=S^+R^{12})(-SR^{13})X^-$;

$Y^{12}$ and $Y^{13}$, independently of one another, denote H or alkyl $R^{12}$ and $R^{13}$, independently of one another, denote an unbranched or branched alkyl radical having 1 to 15 carbon atoms or together form a —$(CH_2)_p$—unit, where p=2, 3, 4, 5 or 6, where one, two or three of these $CH_2$ groups are optionally substituted by at least one unbranched or branched alkyl radical having 1 to 8 carbon atoms; and $X^-$ is a weakly coordinating anion;

comprising converting, in a reaction step (E1), (E1) the compound of the formula ID1

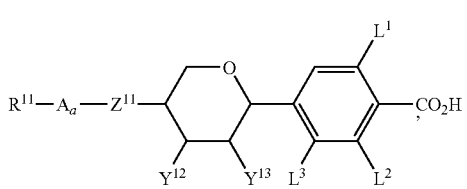

in which $R^{11}$, A, a, $Z^{11}$, $Y^{12}$, and $Y^{13}$ are as defined above for the compound of formula IE, and $L^1$, $L^2$ and $L^3$ denote H, into a compound of formula IE1

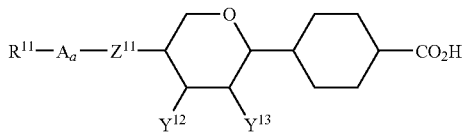

using hydrogen in the presence of a transition-metal catalyst;

and optionally converting, in a reaction step (E2), (E2) the compound of formula IE1 into a compound of formula IE2

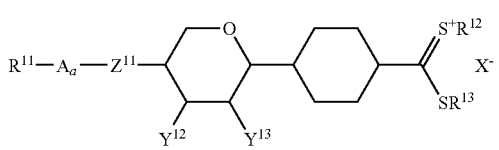

in the presence of an acid HX using $HSR^{12}$ and $HSR^{13}$ or using $HSR^{12}R^{13}SH$.

18. A compound according to claim 1, which is a compound of one of the following formulae

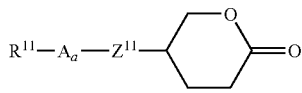
I1

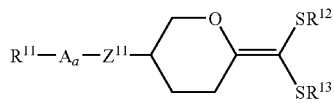
I2

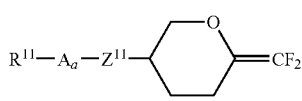
I3

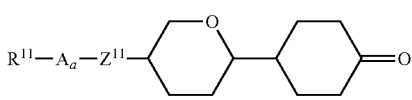
I4

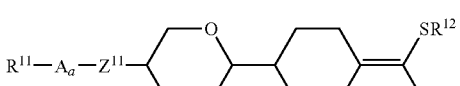
I5

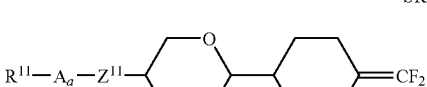
I6

I7

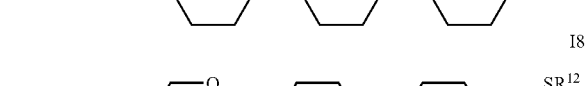
I8

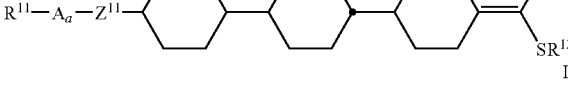
I9

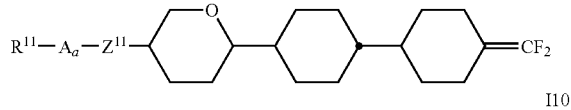
I10

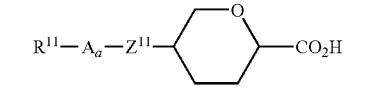
I11

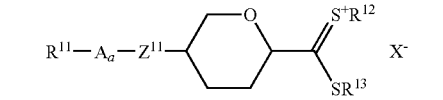
I12

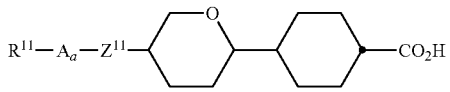
I13

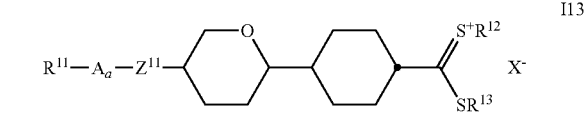
I14

-continued
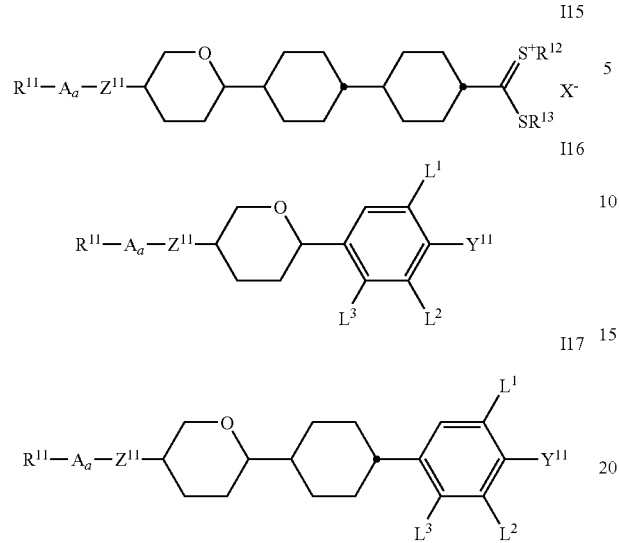
wherein $R^{11}$, A, a, $Z^{11}$, $Y^{11}$, $L^1$, $L^2$, $L^3$, $R^{12}$, $R^{13}$ and $X^-$ have the meanings indicated for the compound of formula I.
19. A compound according to claim 1, which is a compound of one of the following formulae
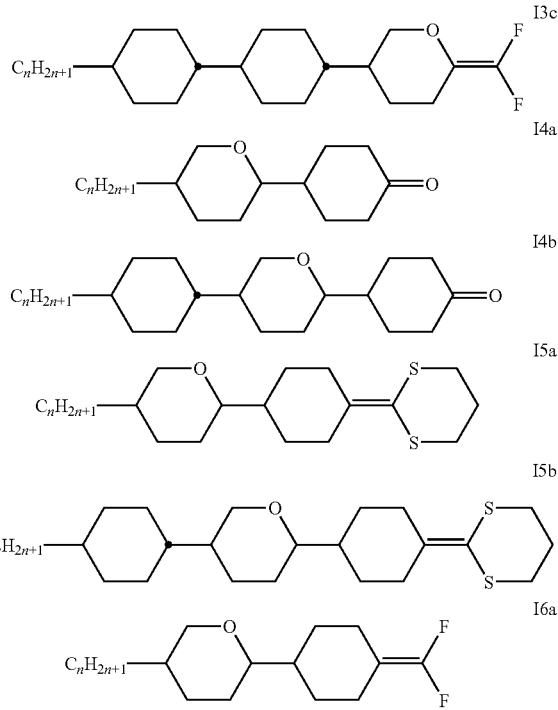
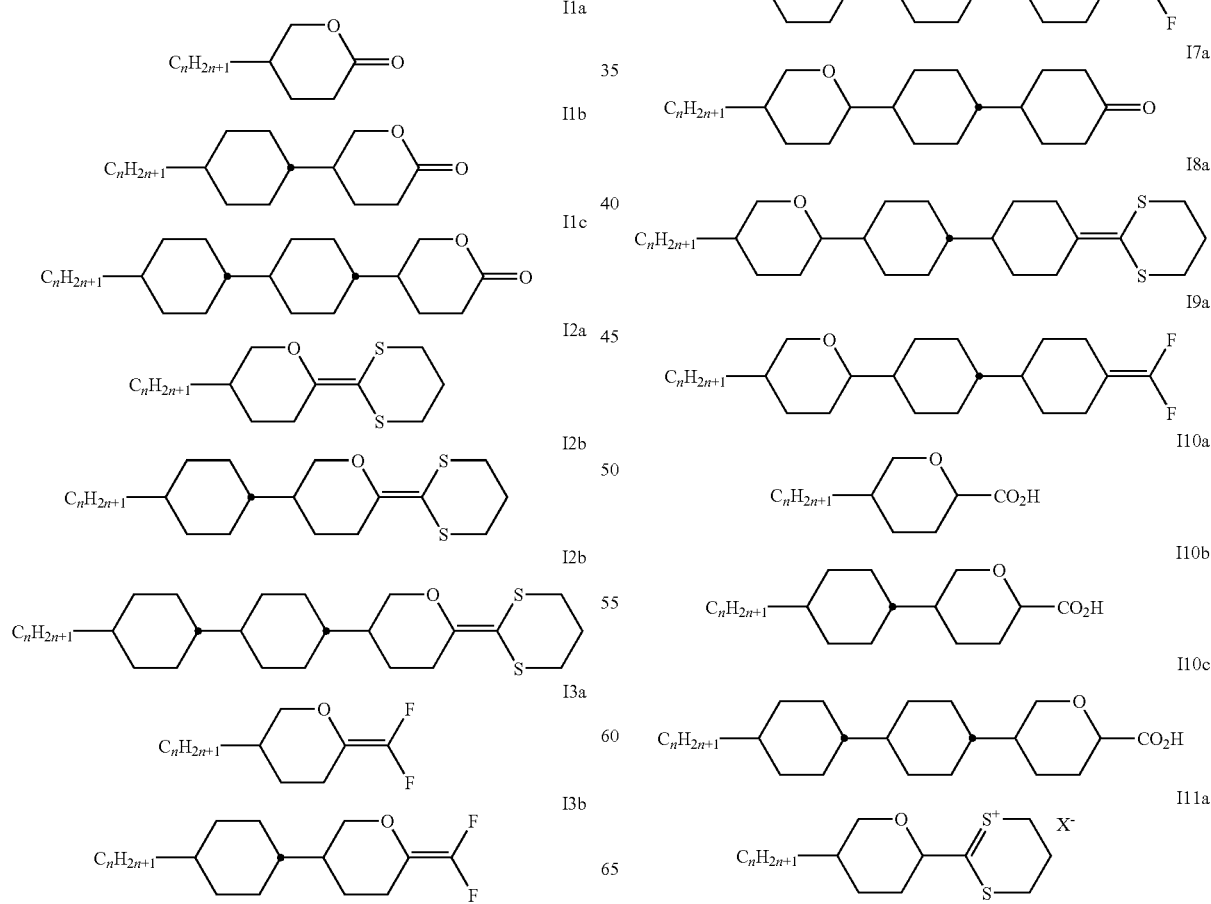

-continued
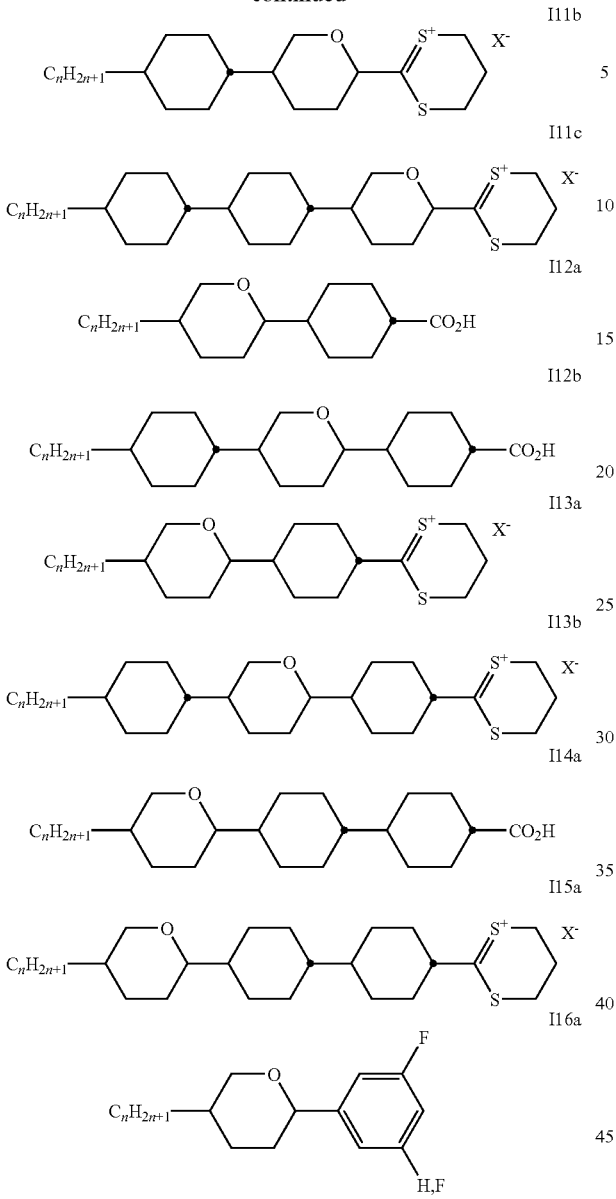
-continued
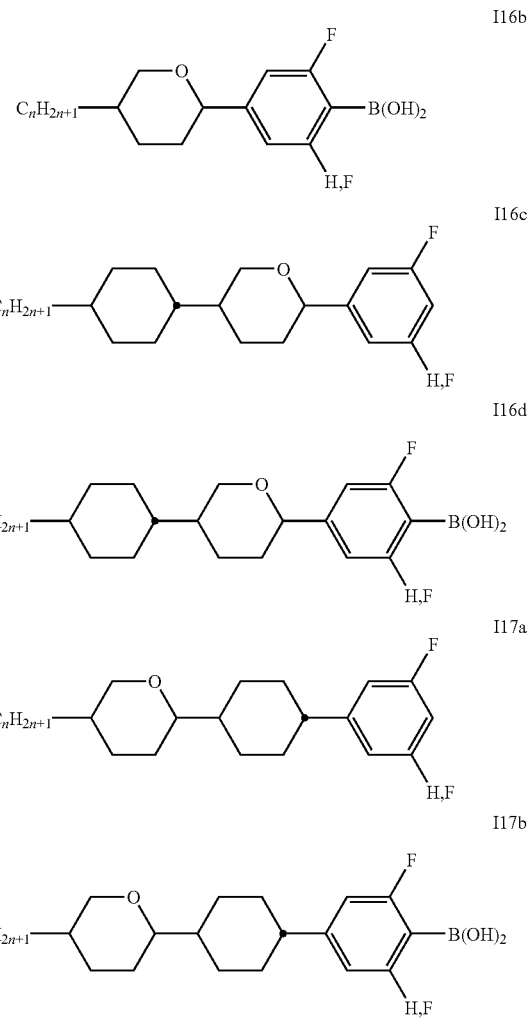
wherein n is an integer of 1 to 7.
20. A compound according to claim 10, wherein $C_nH_{2n+1}$ is straight-chain.
* * * * *

UNITED STATES PATENT AND TRADEMARK OFFICE
CERTIFICATE OF CORRECTION

PATENT NO. : 7,638,641 B2  Page 1 of 1
APPLICATION NO. : 10/536803
DATED : December 29, 2009
INVENTOR(S) : Peer Kirsch et al.

It is certified that error appears in the above-identified patent and that said Letters Patent is hereby corrected as shown below:

Title page, item (*) Notice: should read as follows:

Subject to any disclaimer, the term of this patent is extended or adjusted under 35 U.S.C. 154(b) by 1191 days.

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,638,641 B2  Page 1 of 2
APPLICATION NO. : 10/536803
DATED : December 29, 2009
INVENTOR(S) : Kirsch et al.

It is certified that error appears in the above-identified patent and that said Letters Patent is hereby corrected as shown below:

Column 26, lines 32 - 67 delete, "then $Y^{11}$ denotes -H, -I, -SH, -CO$_2$R,$^{14}$ -OSO$_2$R$^{15}$, -C(=S$^+$R$^{12}$)(SR$^{13}$)X$^-$, -B(OR$^{16}$)(OR$^{17}$), -BF$_3^-$Cat$^+$, -Si(OR$^{18}$)(OR$^{19}$)(OR$^{20}$) or alkyl, where alkyl denotes a halogenated or unsubstituted alkyl radical having 1 to 15 C atoms, in which one or more CH$_2$ groups have each been replaced, independently of one another, by -C≡C-, -CH=CH-, -O-, -CO-, -CO-O- or -O-CO- in such a way that O atoms are not linked directly to one another and alkyl does not stand for alkoxy; if W is connected directly to

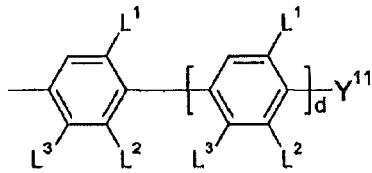

where
d is 0 or 1;
then B does not stand for;

if d=1; and
that A can adopt identical or different meanings if a is 2:"

Signed and Sealed this

Twenty-ninth Day of June, 2010

David J. Kappos
*Director of the United States Patent and Trademark Office* insert --then $Y^{11}$ does not denote =O, =C(SR$^{12}$)(SR$^{13}$) or =CF$_2$;

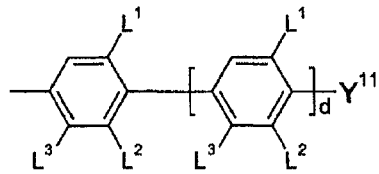, if W is connected directly to where d is 0 or 1, then $Y^{11}$ denotes -H, -I, -SH, -CO$_2$R$^{14}$, -OSO$_2$R$^{15}$, -C(=S$^+$R$^{12}$)(SR$^{13}$)X$^-$, -B(OR$^{16}$)(OR$^{17}$), -BF$_3^-$Cat$^+$, -Si(OR$^{18}$)(OR$^{19}$)(OR$^{20}$) or alkyl, where alkyl denotes a halogenated or unsubstituted alkyl radical having 1 to 15 C atoms, in which one or more CH$_2$ groups have each been replaced, independently of one another, by -C≡C-, -CH=CH-, -O-, -CO-, -CO-O- or -O-CO- in such a way that O atoms are not linked directly to one another and alkyl does not stand for alkoxy;

if d=1, then B does not stand for

 ; and if a is 2, then that A can adopt identical or different meanings.--